United States Patent
Robison et al.

(10) Patent No.: US 12,421,561 B2
(45) Date of Patent: Sep. 23, 2025

(54) COMPOSITION, METHOD, AND SYSTEM FOR A RAPID, REAL-TIME PENTAPLEX PCR ASSAY FOR MAJOR BETA-LACTAMASE GENES

(71) Applicant: Brigham Young University, Provo, UT (US)

(72) Inventors: Richard A. Robison, Provo, UT (US); Taalin Hoj, Provo, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 166 days.

(21) Appl. No.: 17/670,221

(22) Filed: Feb. 11, 2022

(65) Prior Publication Data

US 2022/0290213 A1 Sep. 15, 2022

Related U.S. Application Data

(60) Provisional application No. 63/148,520, filed on Feb. 11, 2021.

(51) Int. Cl.
*C12Q 1/689* (2018.01)

(52) U.S. Cl.
CPC ......... *C12Q 1/689* (2013.01); *C12Q 2600/16* (2013.01)

(58) Field of Classification Search
CPC ... C12Q 1/689; C12Q 1/6806; C12Q 2600/16
See application file for complete search history.

(56) References Cited

FOREIGN PATENT DOCUMENTS

| WO | WO-2015159068 A1 * | 10/2015 | ............ A61K 35/76 |
|----|---------------------|---------|-------------------------|
| WO | WO-2017218789 A1 * | 12/2017 | ........... C12Q 1/6809 |

OTHER PUBLICATIONS

GenBank Accession No. GU064912. (Year: 2016).*
Pérez-Pérez et al., "Detection of Plasmid-Mediated AmpC-Lactamase Genes in Clinical Isolates by Using Multiplex PCR, " Journal of Clinical Microbiology, vol. 40, No. 6. (Year: 2002).*

* cited by examiner

*Primary Examiner* — Angela M. Bertagna
*Assistant Examiner* — Francesca Filippa Giammona
(74) *Attorney, Agent, or Firm* — NGUYEN TARBET IP LAW

(57) ABSTRACT

Provided herein are a composition, system, and kit for the real-time pentaplex amplification and detection of DNA from at least one of beta-lactamase genes Klebsiella pneumoniae carbapenemase (KPC); New Delhi metallo-beta-lactamase (NDM); cefotaximase-Munich (CTX); cephamycin AmpC beta-lactamase (CMY); and oxacillinase-48 (OXA-48).

8 Claims, 19 Drawing Sheets
(1 of 19 Drawing Sheet(s) Filed in Color)
Specification includes a Sequence Listing.

| | Beta-lactamase Gene* | | | | |
|---|---|---|---|---|---|
| | KPC | NDM | CTX | CMY | OXA-48 |
| Isolate Number | | | | | |
| 0112 | + | | | | |
| 0113 | + | | | | |
| 0114 | + | | | | |
| 0115 | + | | | | |
| 0116 | + | | | + | |
| 0118 | | + | | + | |
| 0119 | | + | + | + | |
| 0120 | + | | | | |
| 0127 | | + | | + | |
| 0137 | | + | + | + | |
| 0149 | | + | | + | |
| 0150 | | + | | + | |
| 0160 | | | | | + |

Table 1. Isolates used to validate assay and resistance genes present in each isolate.

|               | Beta-lactamase Gene* |     |     |     |        |
| ------------- | :---: | :-: | :-: | :-: | :----: |
|               | KPC | NDM | CTX | CMY | OXA-48 |
| Isolate Number |     |     |     |     |        |
| 0112          | +   |     |     |     |        |
| 0113          | +   |     |     |     |        |
| 0114          | +   |     |     |     |        |
| 0115          | +   |     |     |     |        |
| 0116          | +   |     |     | +   |        |
| 0118          |     | +   |     | +   |        |
| 0119          |     | +   | +   | +   |        |
| 0120          | +   |     |     |     |        |
| 0127          |     | +   |     | +   |        |
| 0137          |     | +   | +   | +   |        |
| 0149          |     | +   |     | +   |        |
| 0150          |     | +   |     | +   |        |
| 0160          |     |     |     |     | +      |

Table 1. Isolates used to validate assay and resistance genes present in each isolate.

Figure 1

| | Target | Primer/Probe | Sequence (5'→3') | Product (bp) |
|---|---|---|---|---|
| SEQ ID: 1 | KPC | KPC_F* | CCGTCTAGTTCTGCTGTCTTGTCTCT | 109 |
| SEQ ID: 2 | | KPC_R | GCCAAAGTCCTGTTCGAGTTTAGCG | |
| SEQ ID: 3 | | KPC_Pro | FAM-GCTGGCTTTTCTGCCACCGCGCTGACCAA-BHQ1 | |
| SEQ ID: 4 | NDM | NDM_F | GGTTTGATCGTCAGGGATGGCG | 107 |
| SEQ ID: 5 | | NDM_R | GGCAGGTTGATCTCCTGCTTGAT | |
| SEQ ID: 6 | | NDM_Pro | Cy5-TGCTGGTGGTCGATACCGCCTGGACCGATGAC-IBRQ | |
| SEQ ID: 7 | CTX | CTX_F | GTGTGCCGCTGTATGCGC | 127 |
| SEQ ID: 8 | | CTX_R | GCACGATAAAGTATTTGCGAATTATCTGCTGTG | |
| SEQ ID: 9 | | CTX_Pro | Cy3-GCCGAATTAGAGCGGCAGTCGGGAGGCAGA-IBRQ | |
| SEQ ID: 10 | CMY | CMY_F | AGCGACTTTACGCTAACTCCAGCA | 91 |
| SEQ ID: 11 | | CMY_R | CGTCTGGTCATTGCCTCTTCGTAACTC | |
| SEQ ID: 12 | | CMY_Pro | JOE-TGGCGCGCTGGCGGTGAAACCC-BHQ1 | |
| SEQ ID: 13 | OXA-48 | OXA_F | GATATCGCCACTTGGAATCGCGATC | 134 |
| SEQ ID: 14 | | OXA_R | CCATAATCGAAAGCATGTAGCATCTTGCTC | |
| SEQ ID: 15 | | OXA_Pro | TEX615-TTGCCCGCCAAATTGGCGAGGCACGT-BHQ2 | |

Table 2. Pentaplex primer and probe sequences.

Figure 2

|  | Beta-lactamase gene | | | | |
|---|---|---|---|---|---|
|  | KPC | NDM | CTX | CMY | OXA-48 |
| Source |  |  |  |  |  |
| Culture, singleplex | $r^2 = .999$ | $r^2 = 1.000$ | $r^2 = .994$ | $r^2 = 1.000$ | $r^2 = .999$ |
| Culture, pentaplex | $r^2 = .999$ | $r^2 = .998$ | $r^2 = .999$ | $r^2 = .998$ | $r^2 = .999$ |
| Blood, pentaplex; all target genes present | $r^2 = .994$ | $r^2 = .993$ | $r^2 = 1.000$ | $r^2 = 1.000$ | $r^2 = .993$ |
|  |  |  |  |  |  |
| Sensitivity | 4 CFU/ml | 8 CFU/ml | 8 CFU/ml | 8 CFU/ml | 4 CFU/ml |

Table 3. $r^2$ values and sensitivities of each gene from culture in singleplex and pentaplex, or pentaplex from blood.

Figure 3

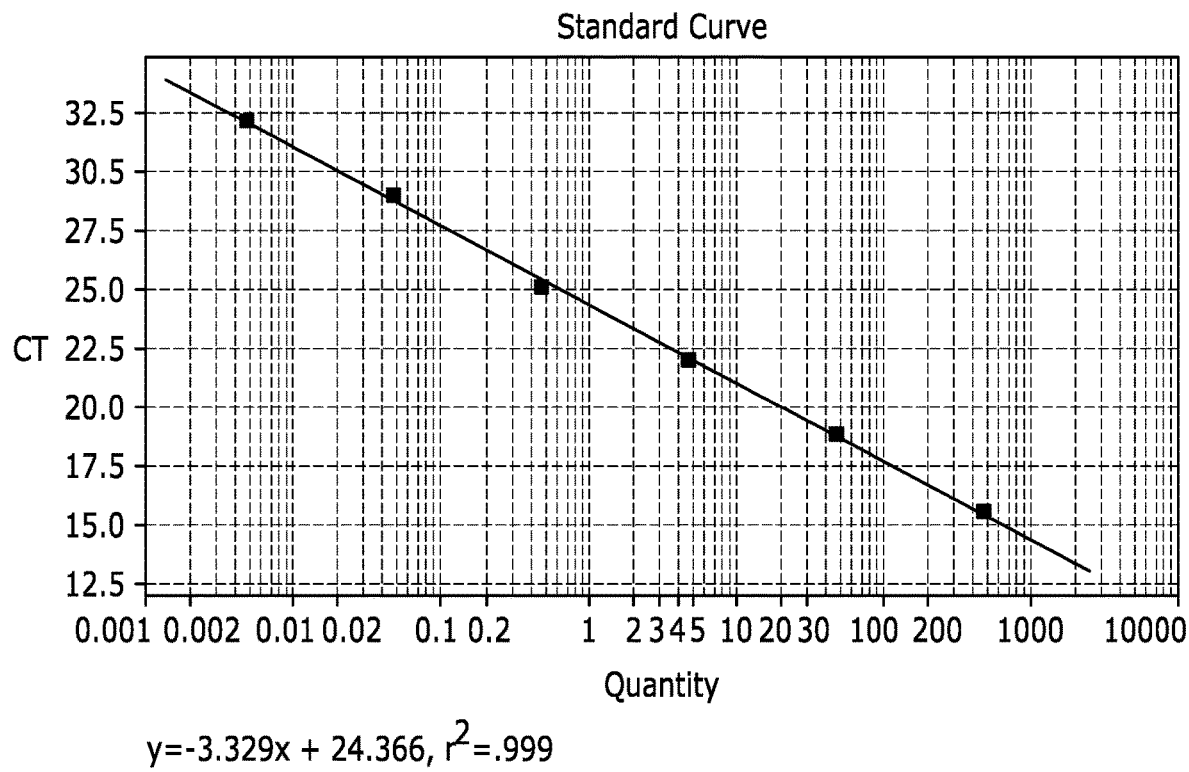
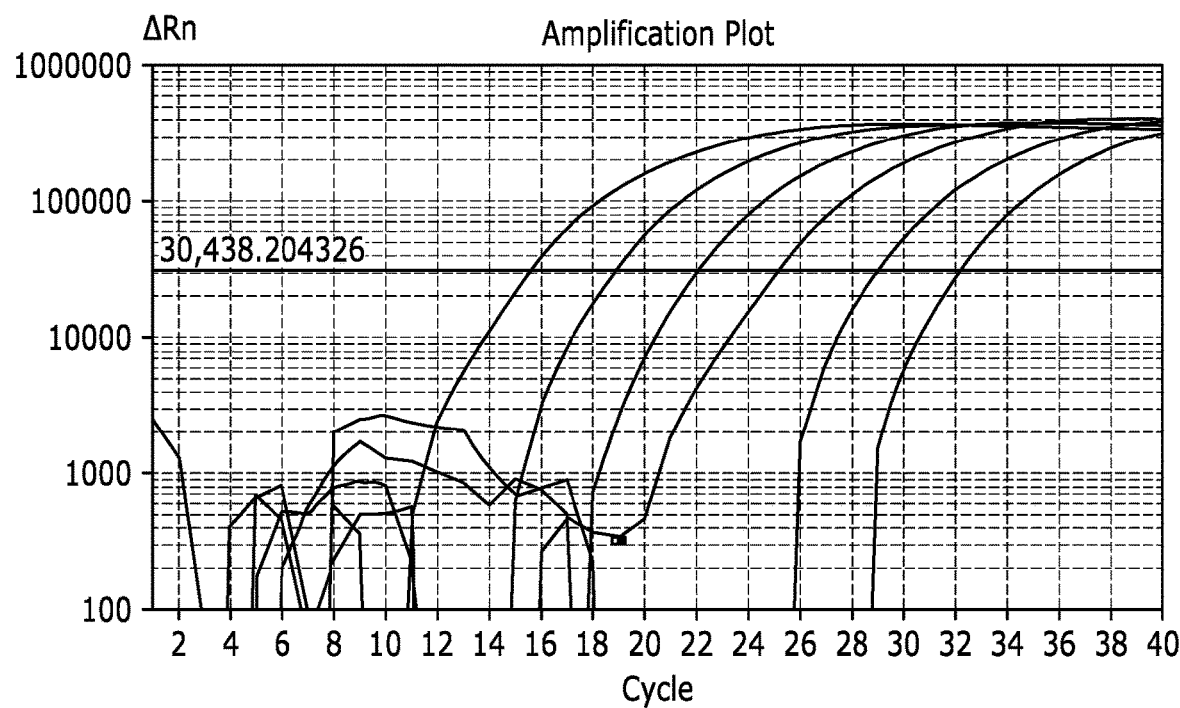
FIG. 4A

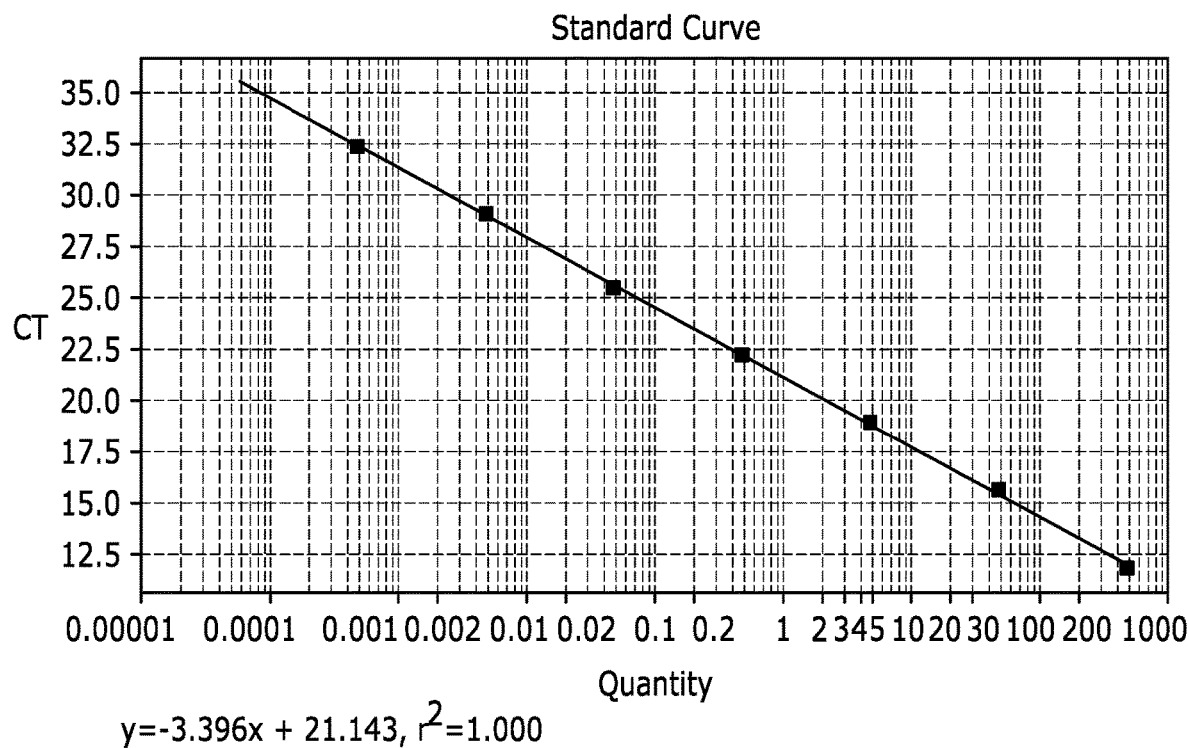
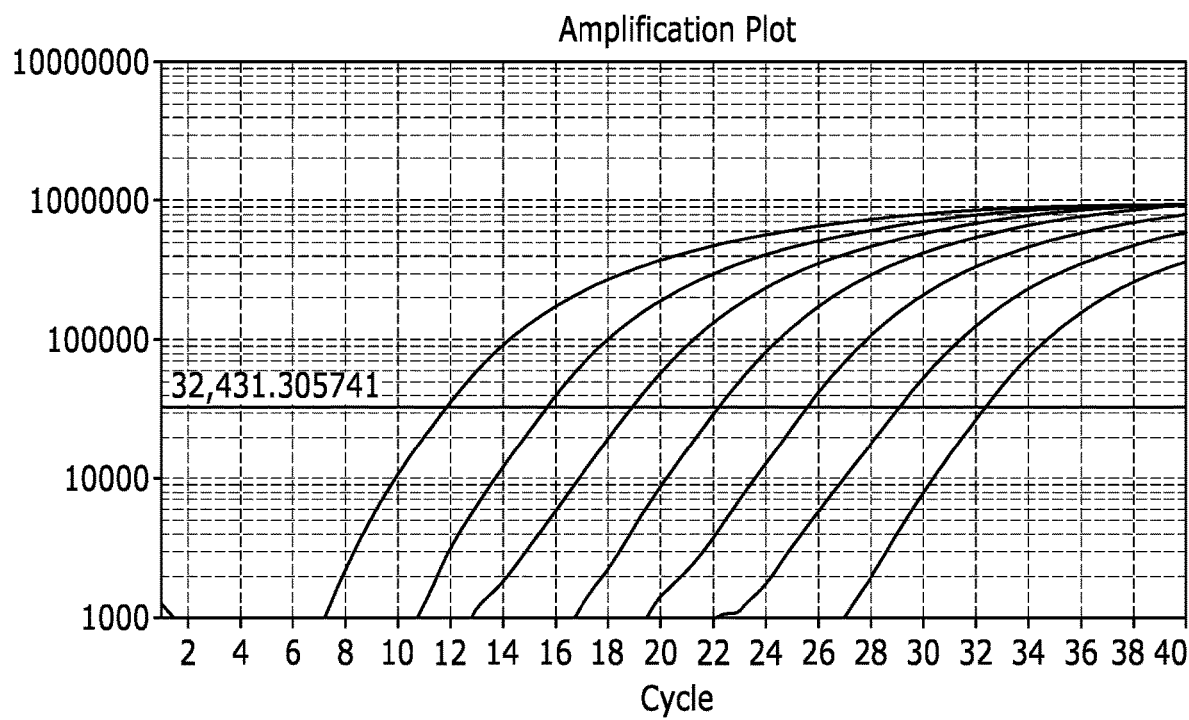
FIG. 4B

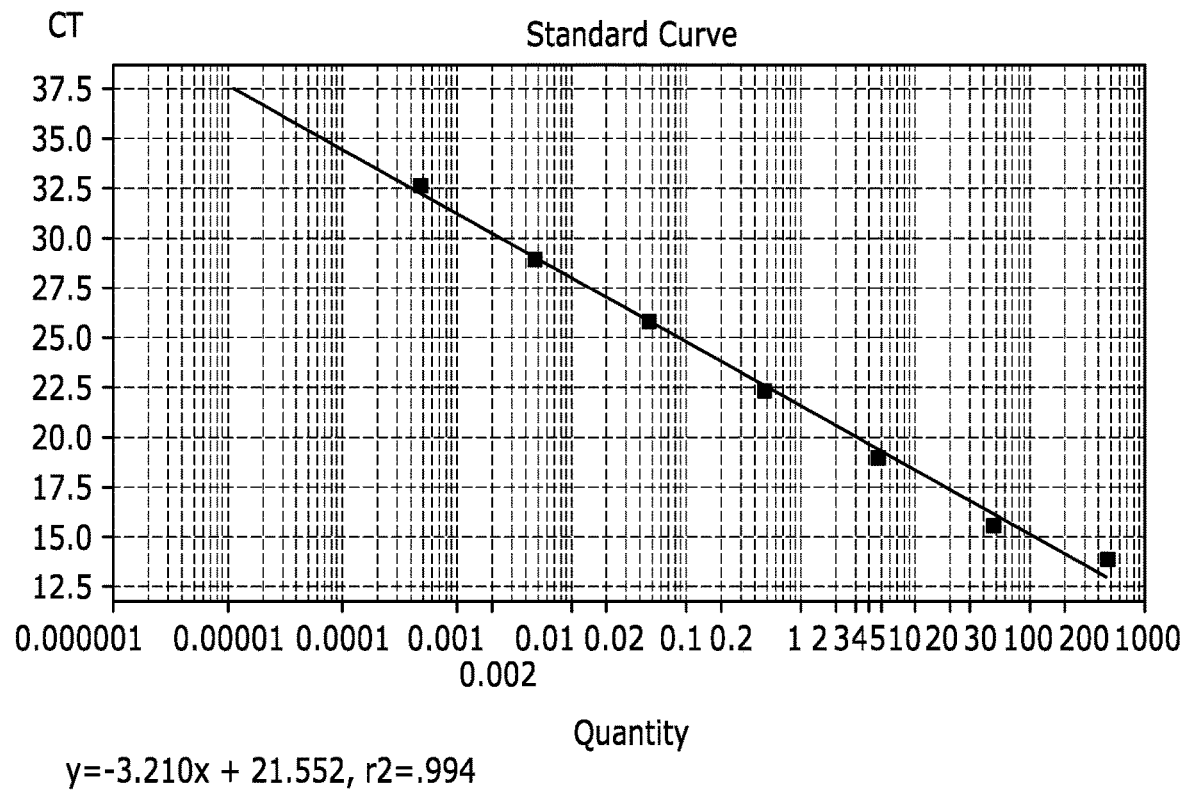
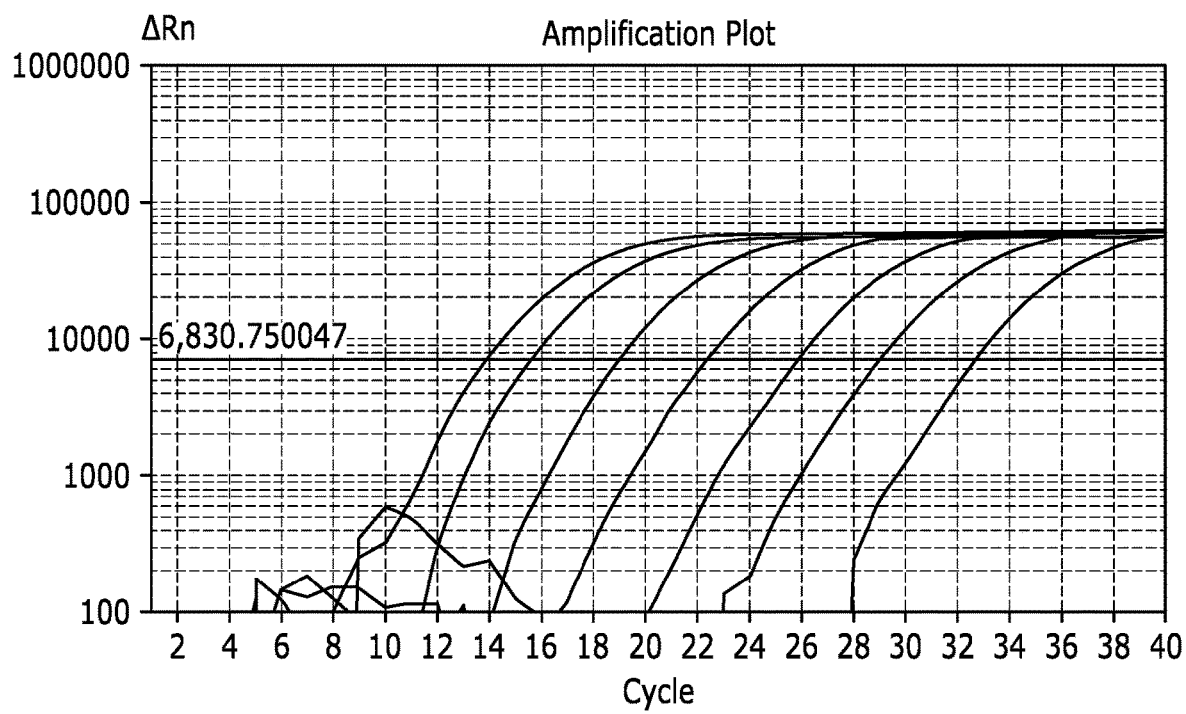
FIG. 4C

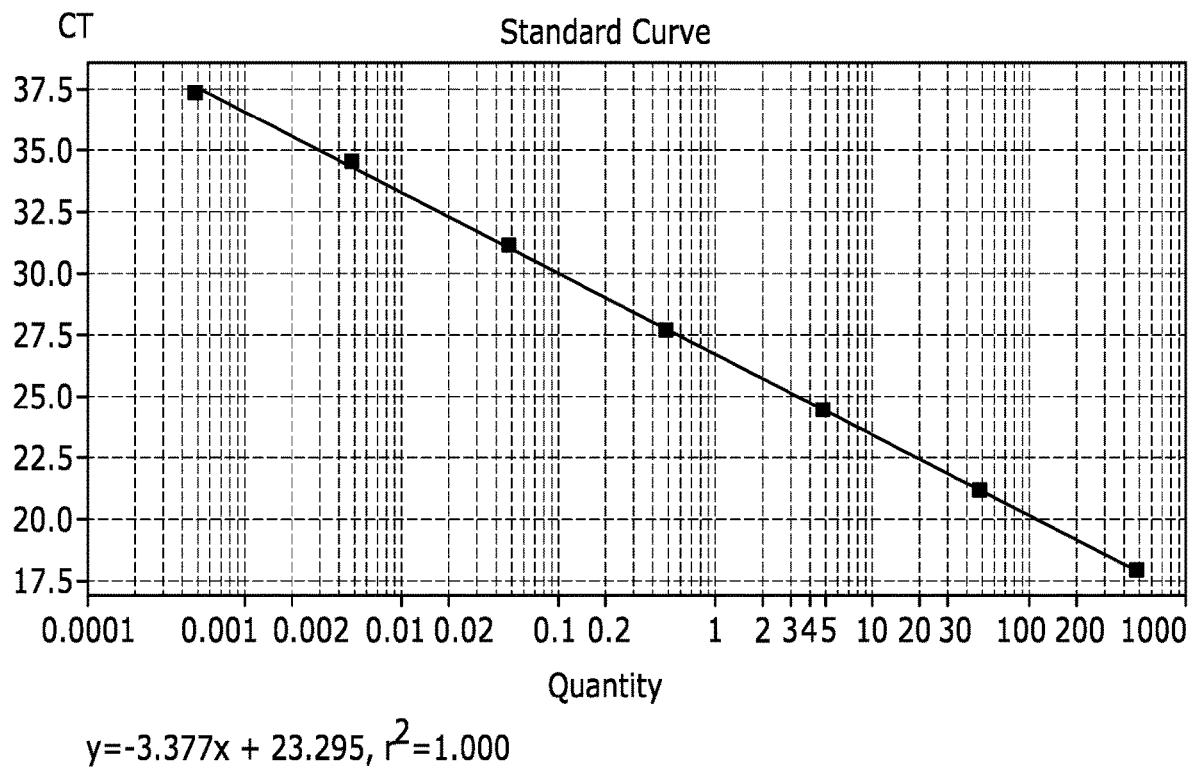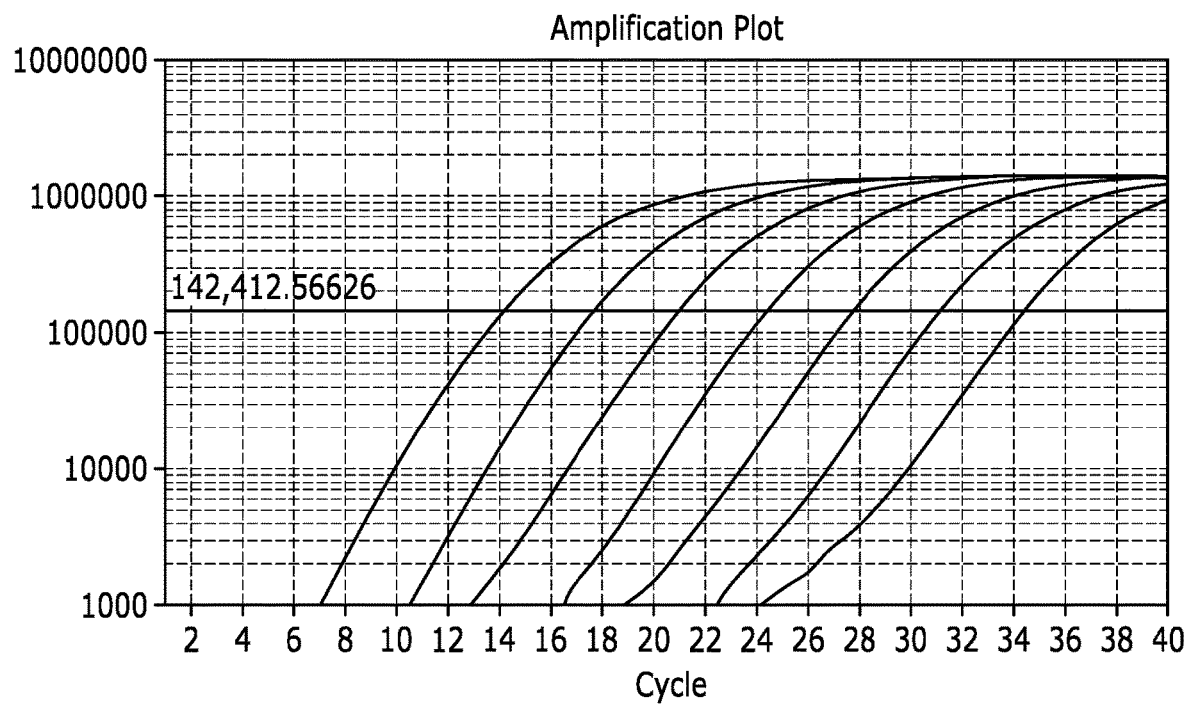
FIG. 4D

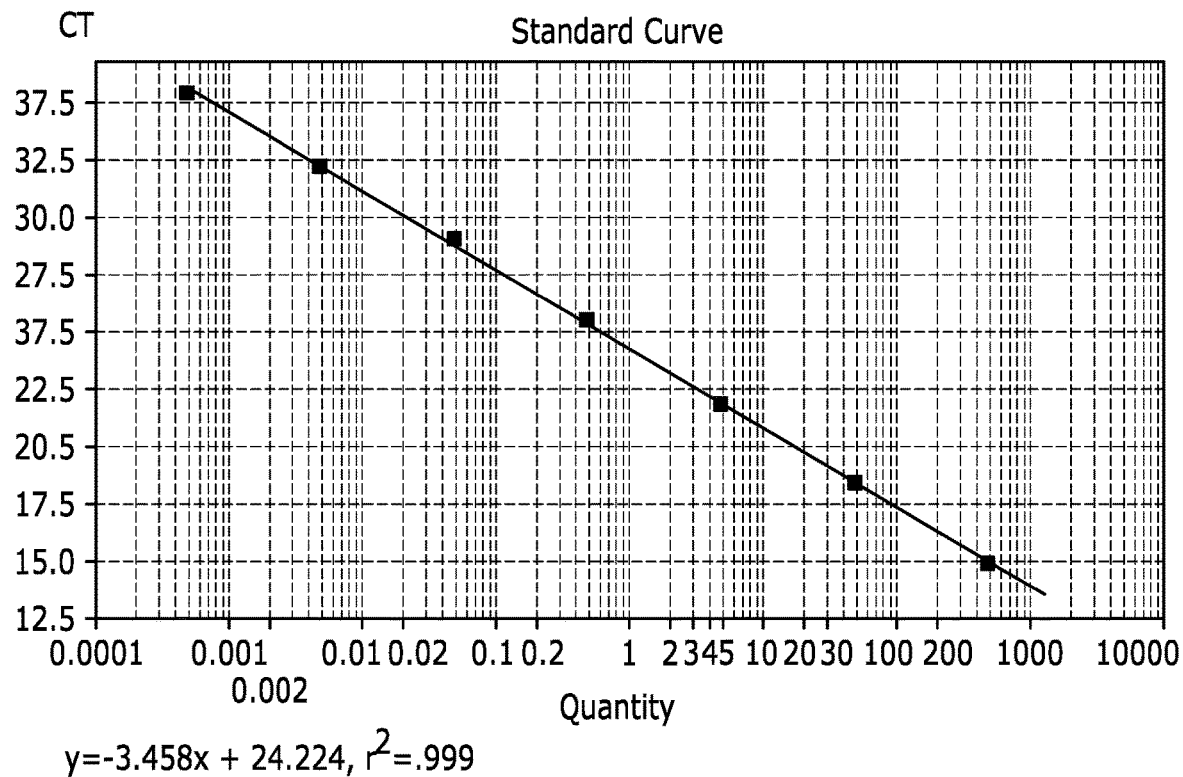
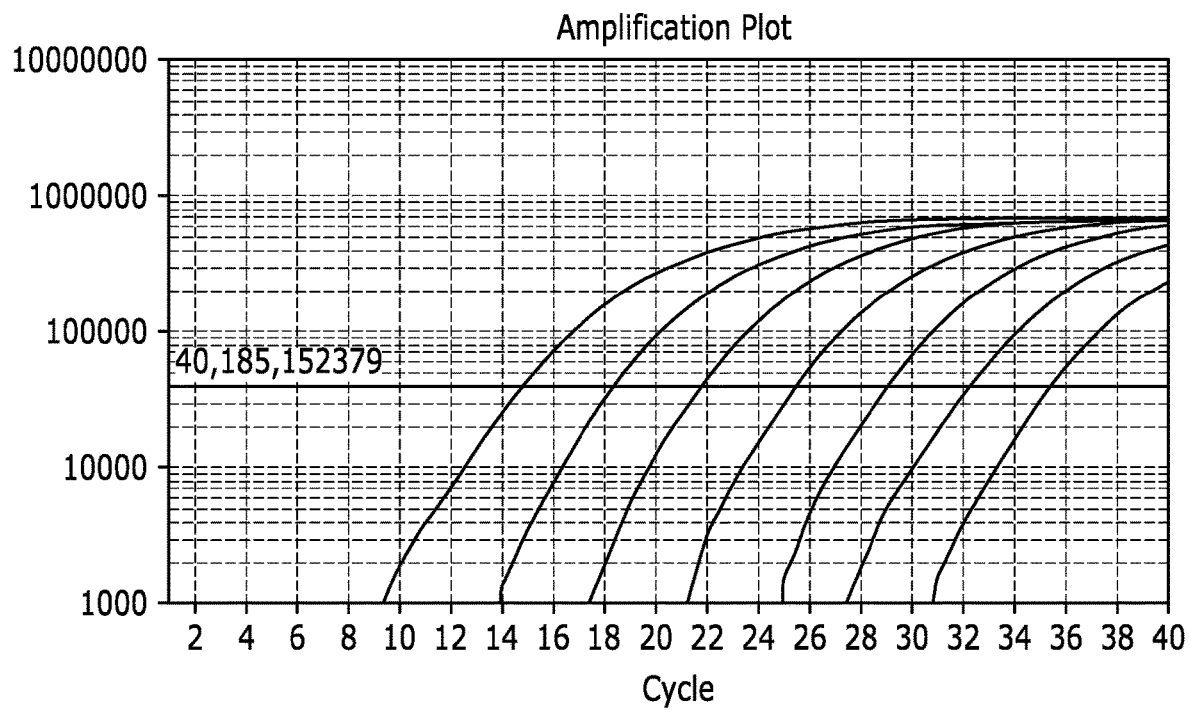
FIG. 4E

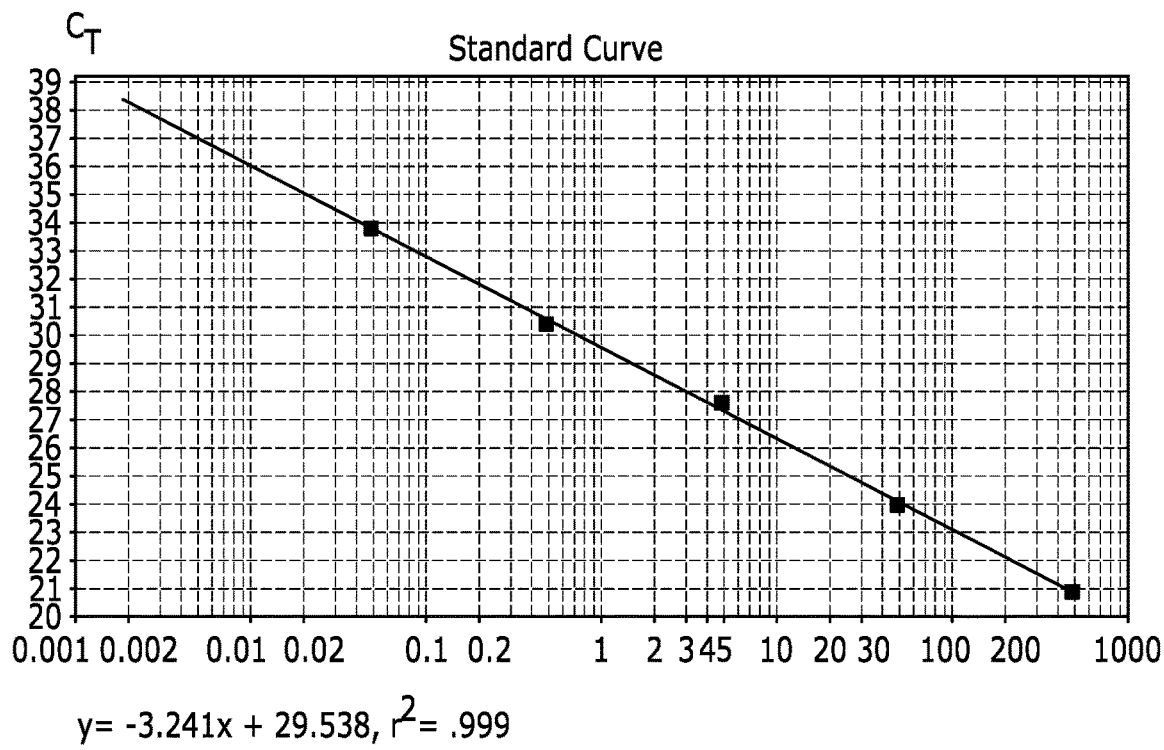
$y = -3.241x + 29.538, r^2 = .999$
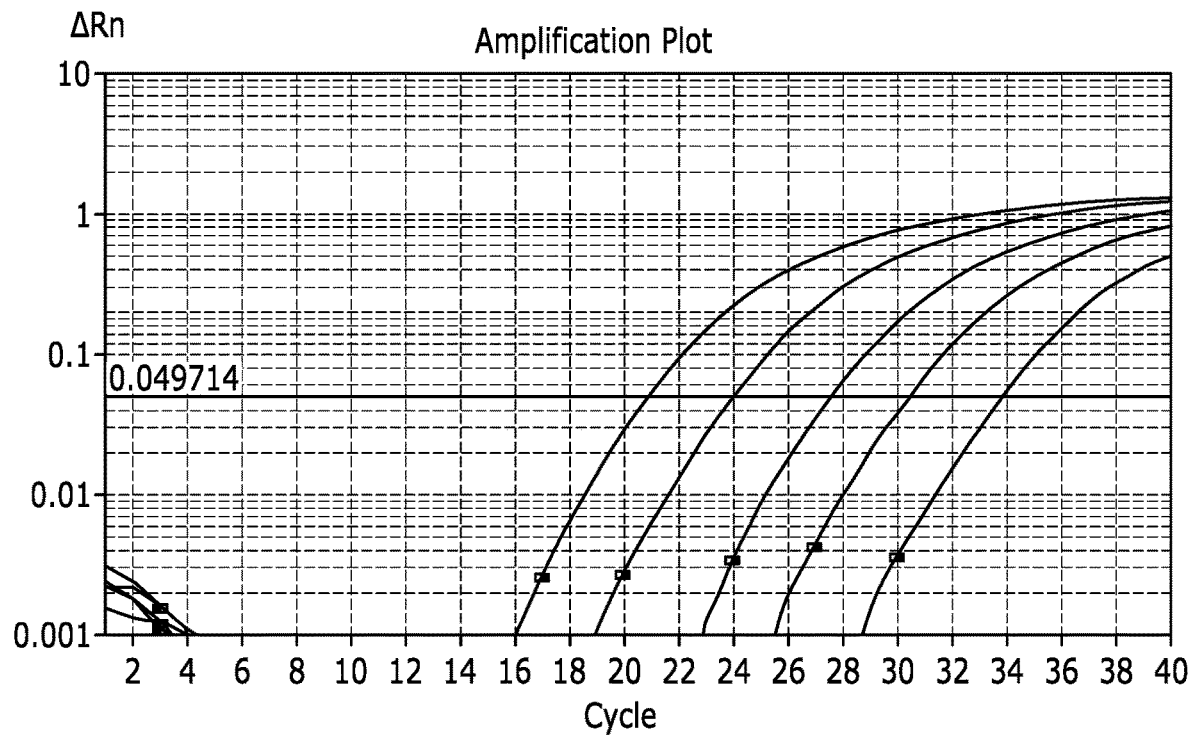
FIG. 5A

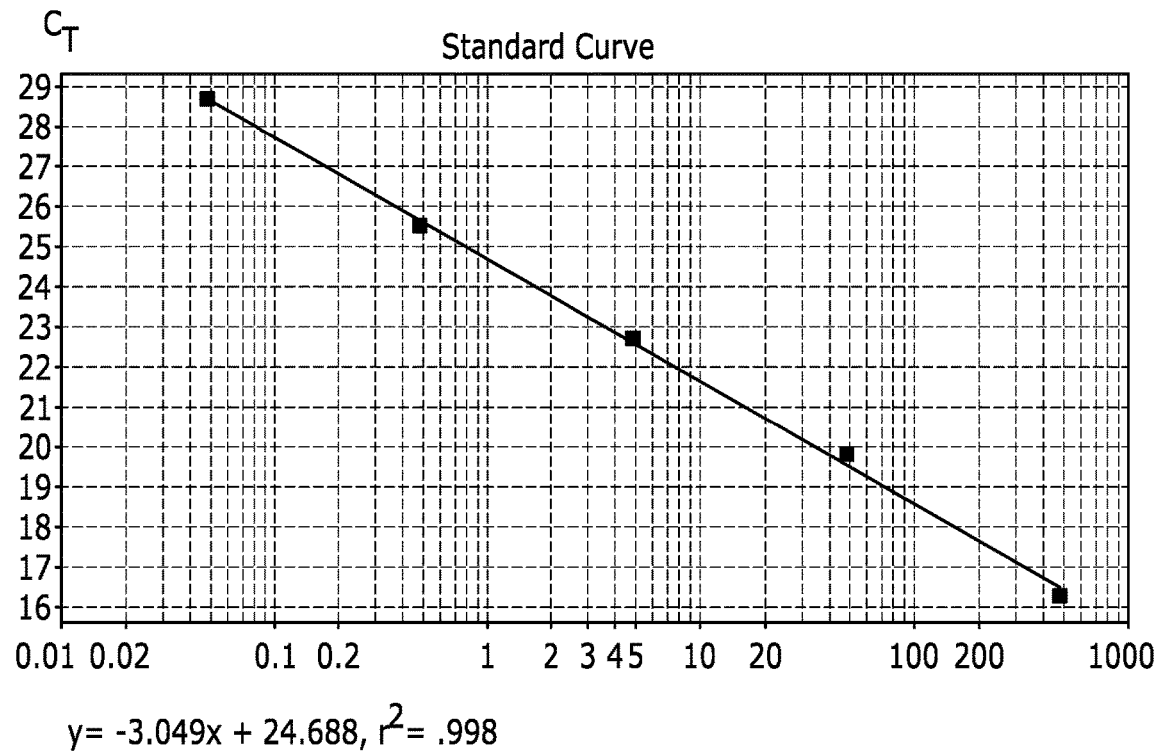
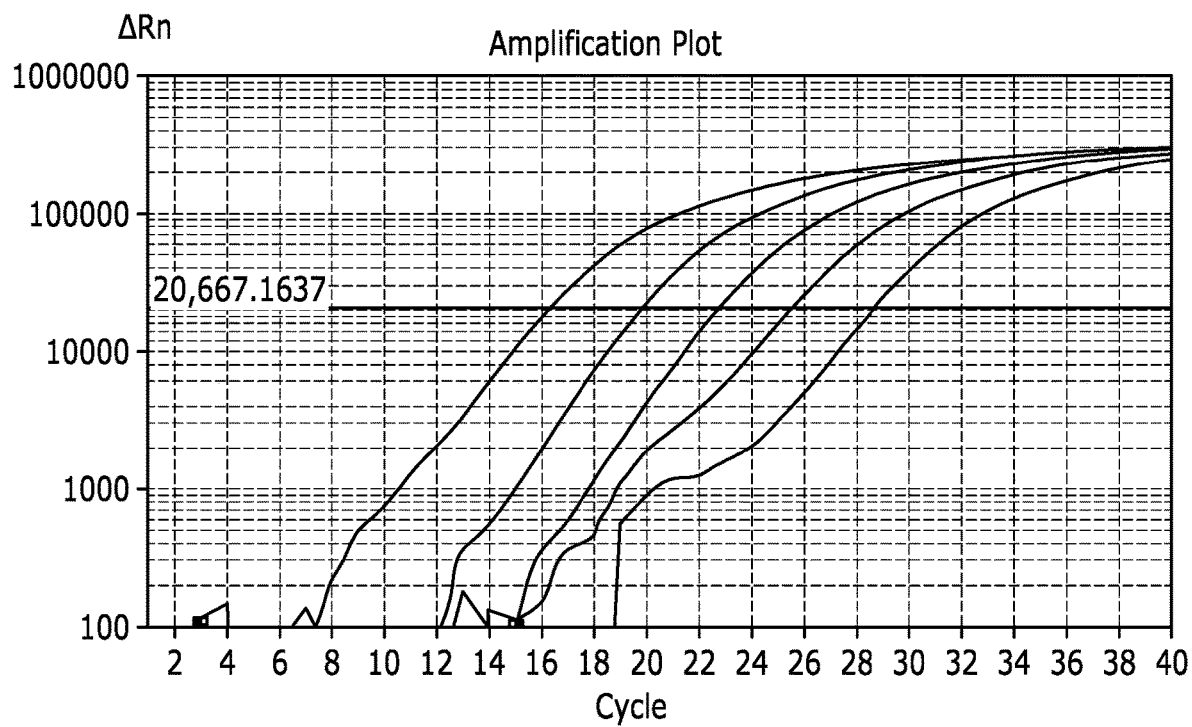
FIG. 5B

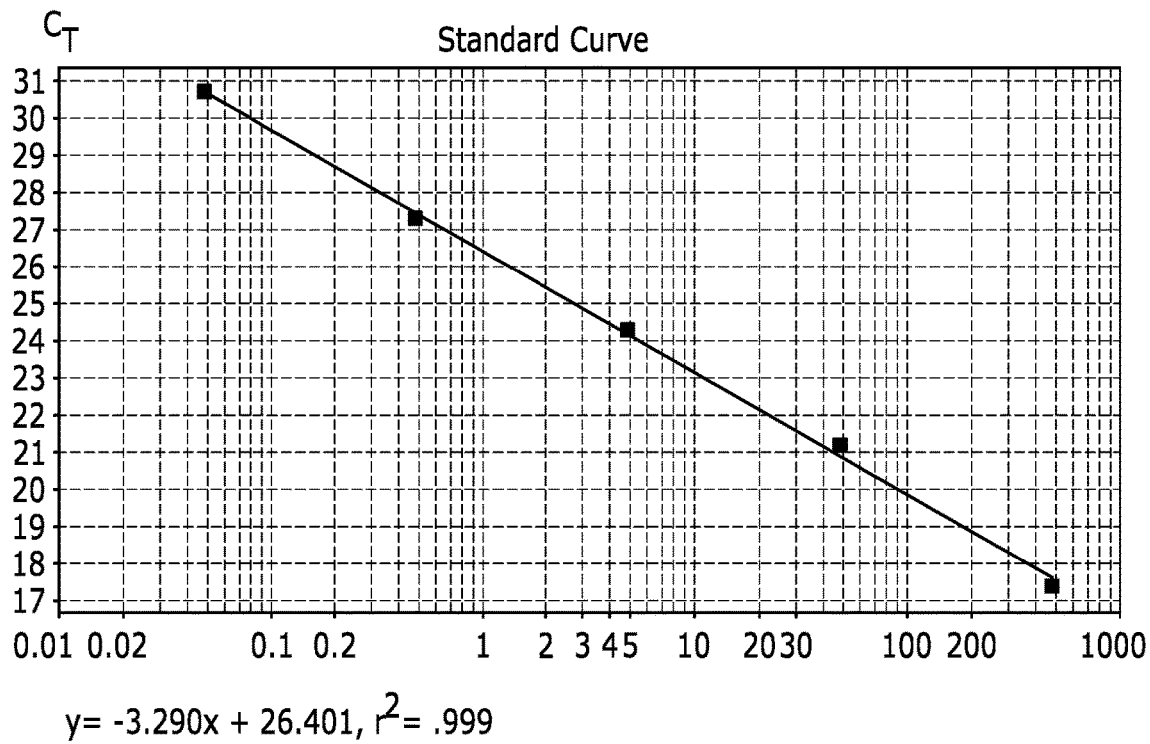
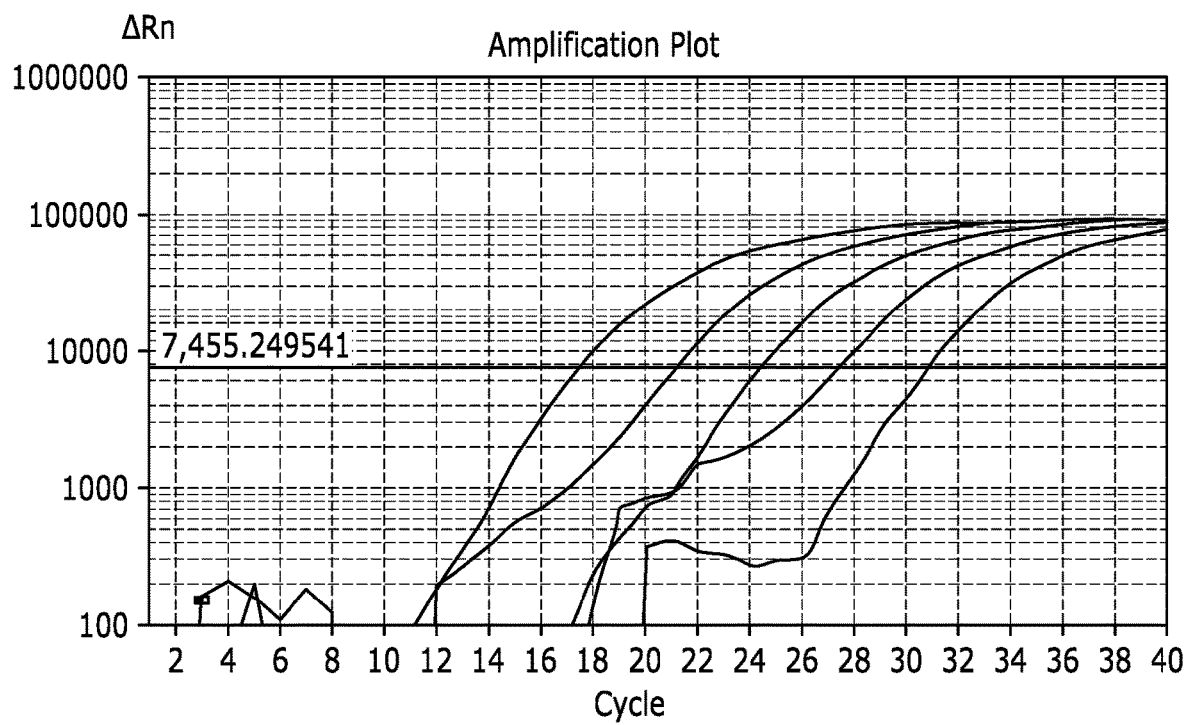
FIG. 5C

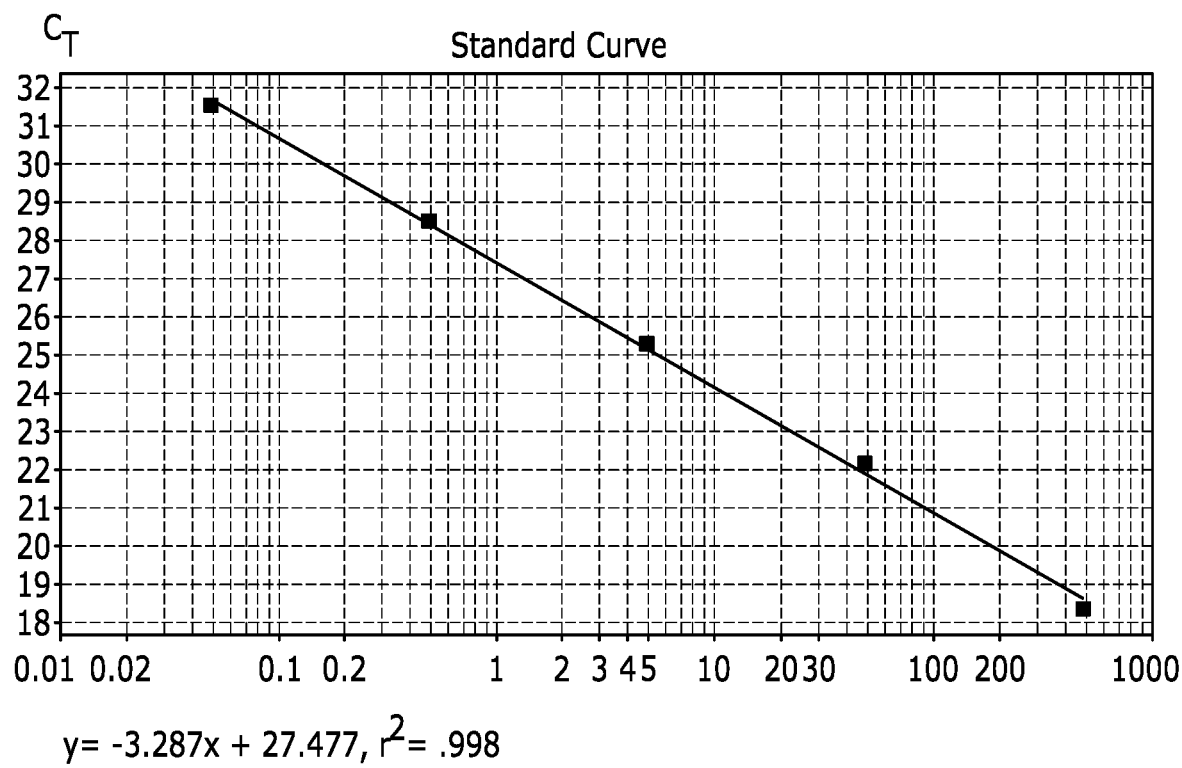
$y = -3.287x + 27.477, r^2 = .998$
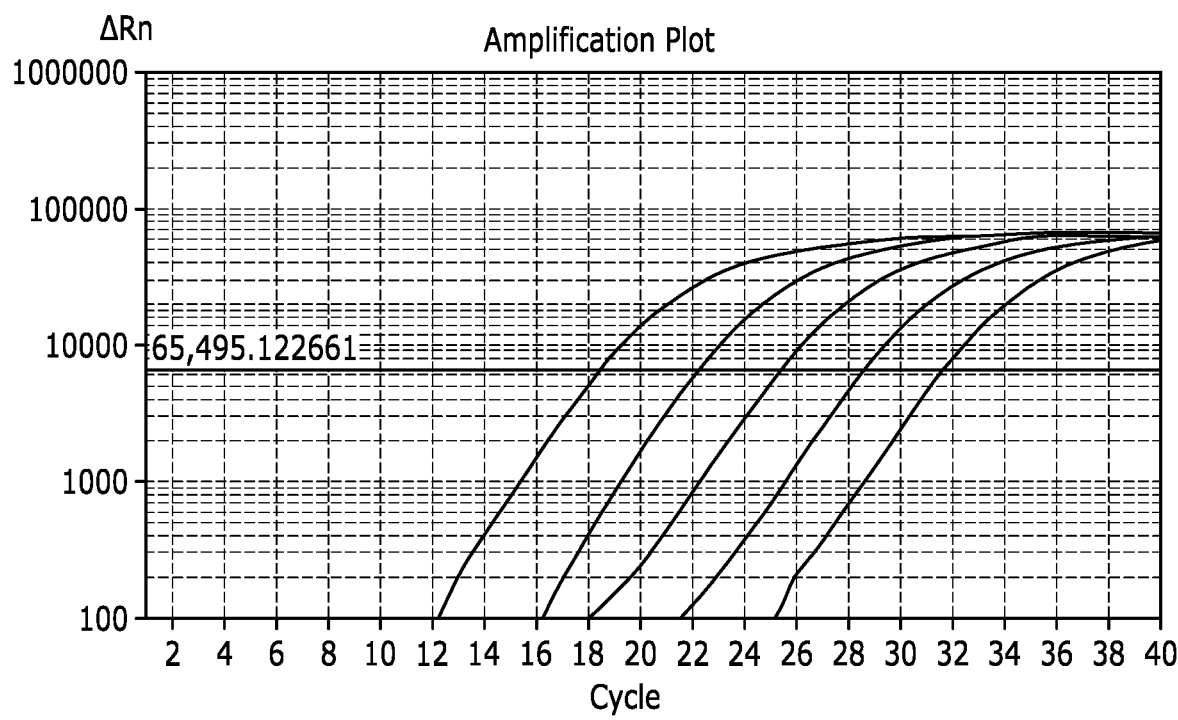
FIG. 5D

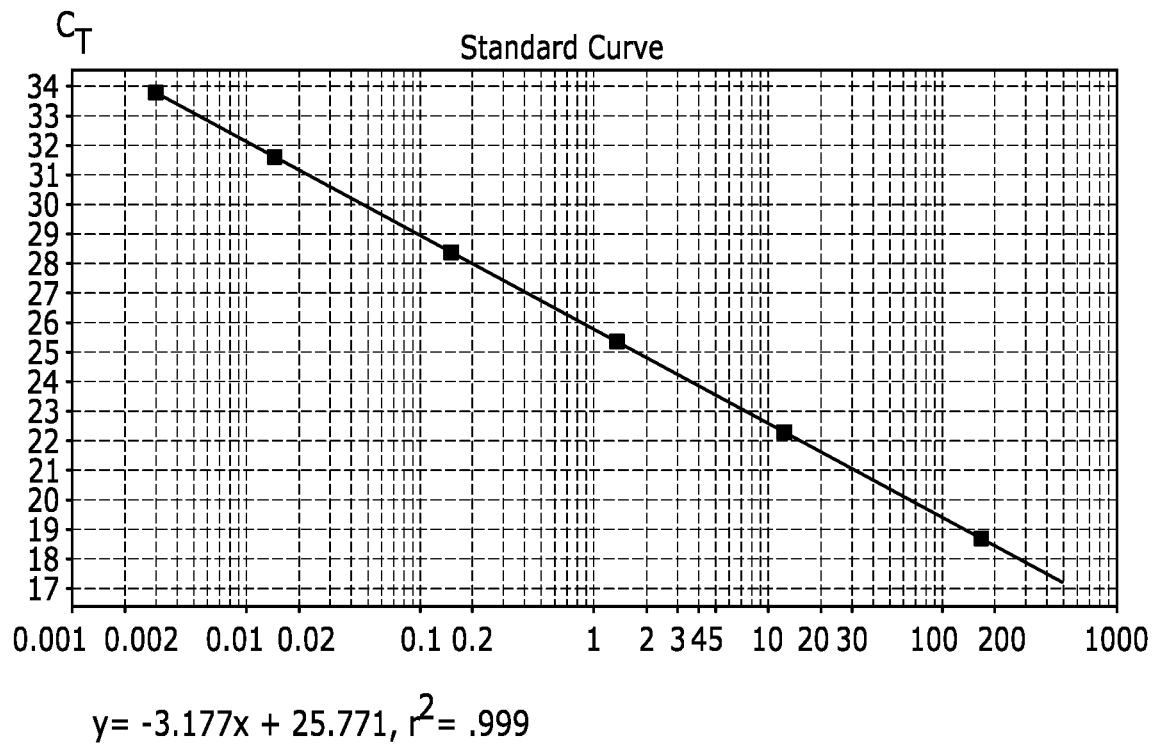
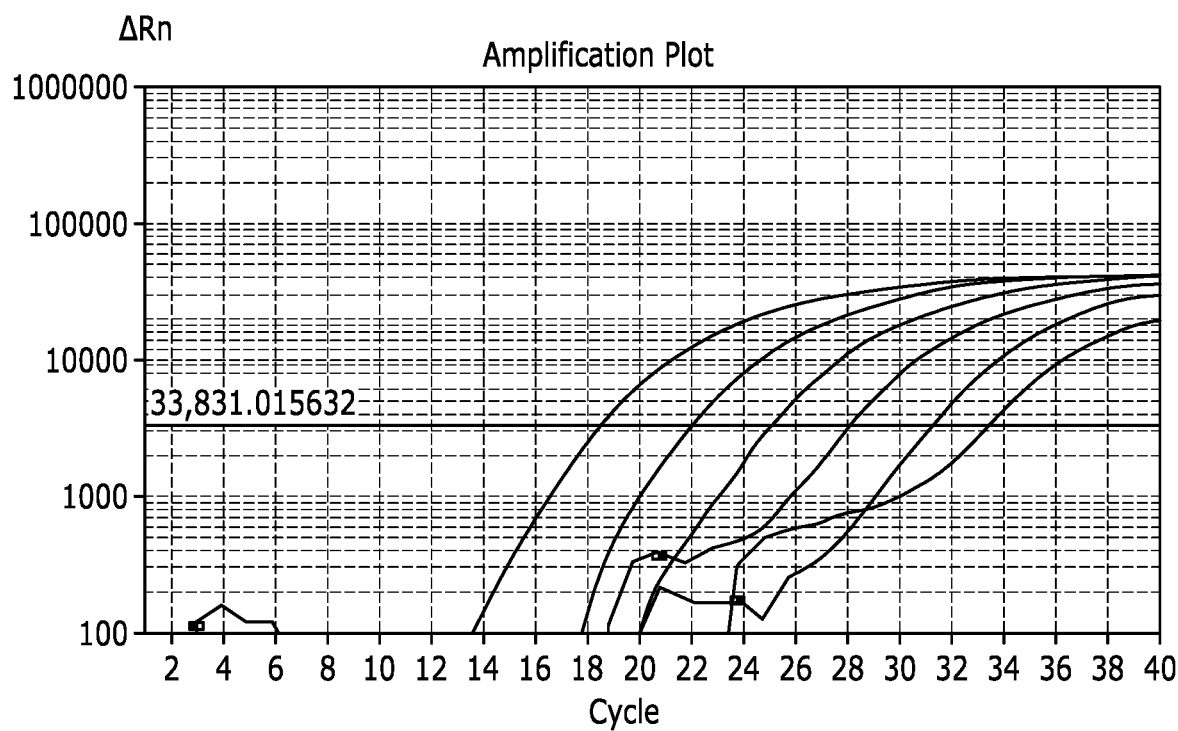
FIG. 5E

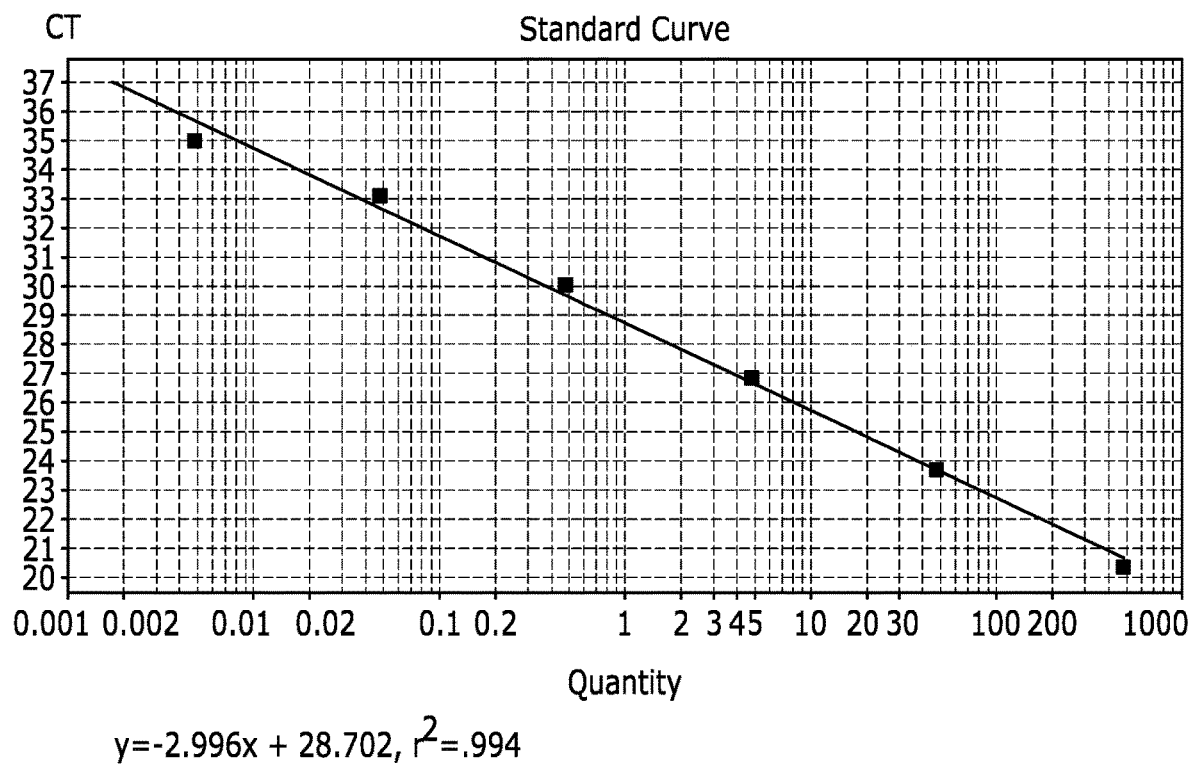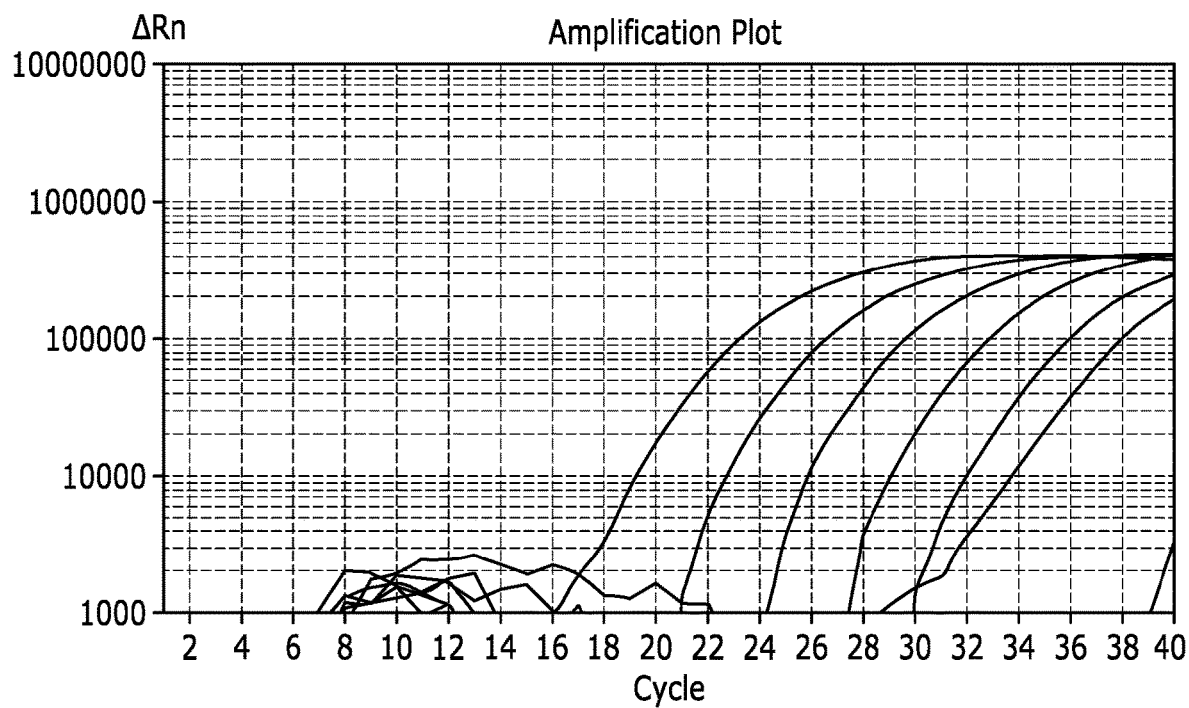
FIG. 6A

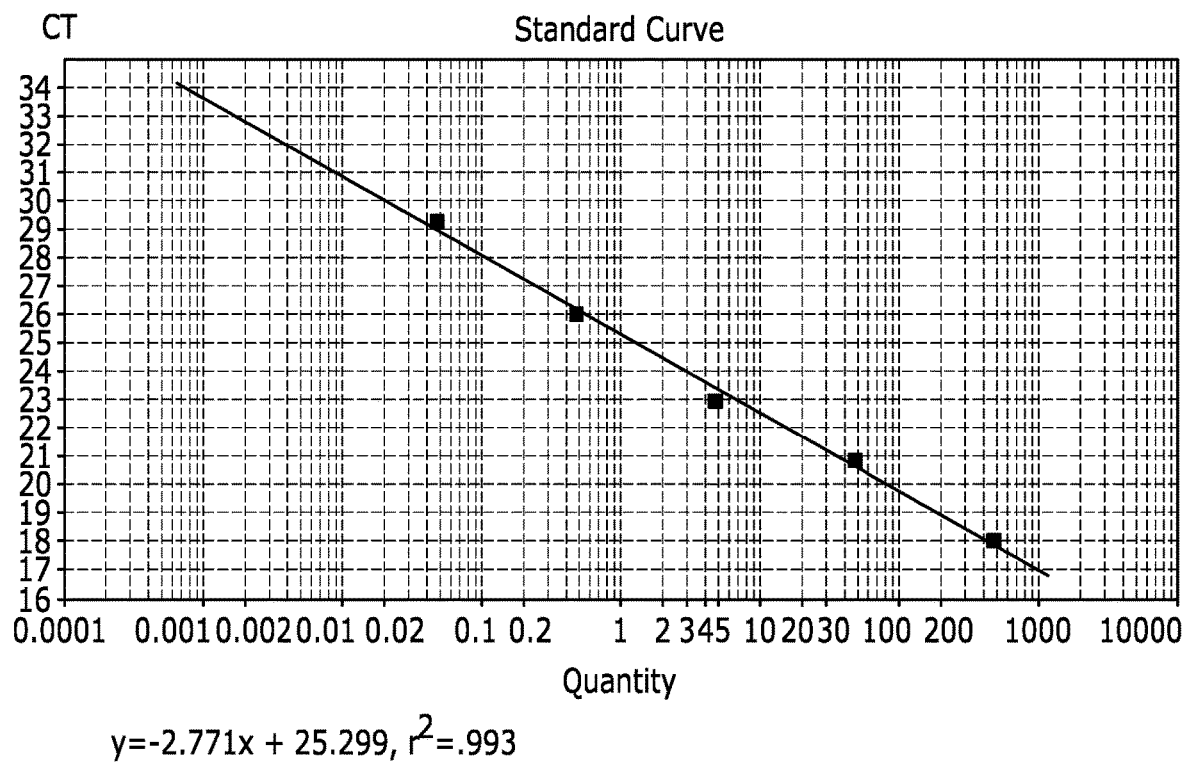
$y = -2.771x + 25.299, r^2 = .993$
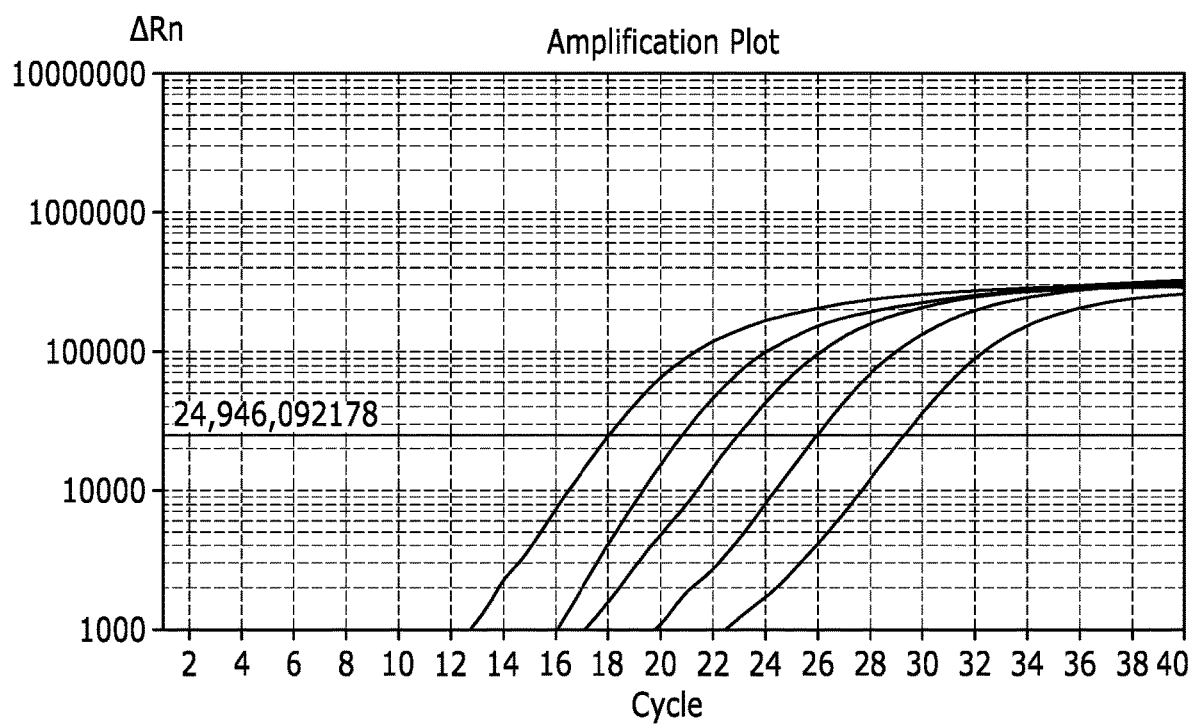
FIG. 6B

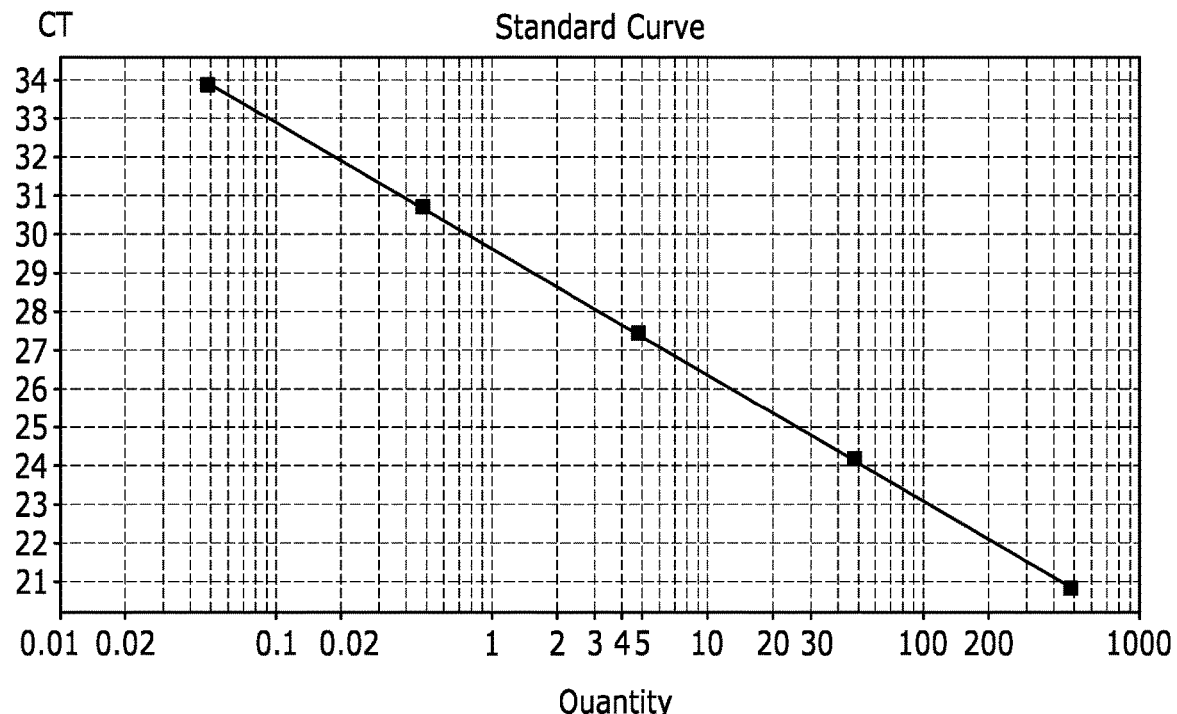
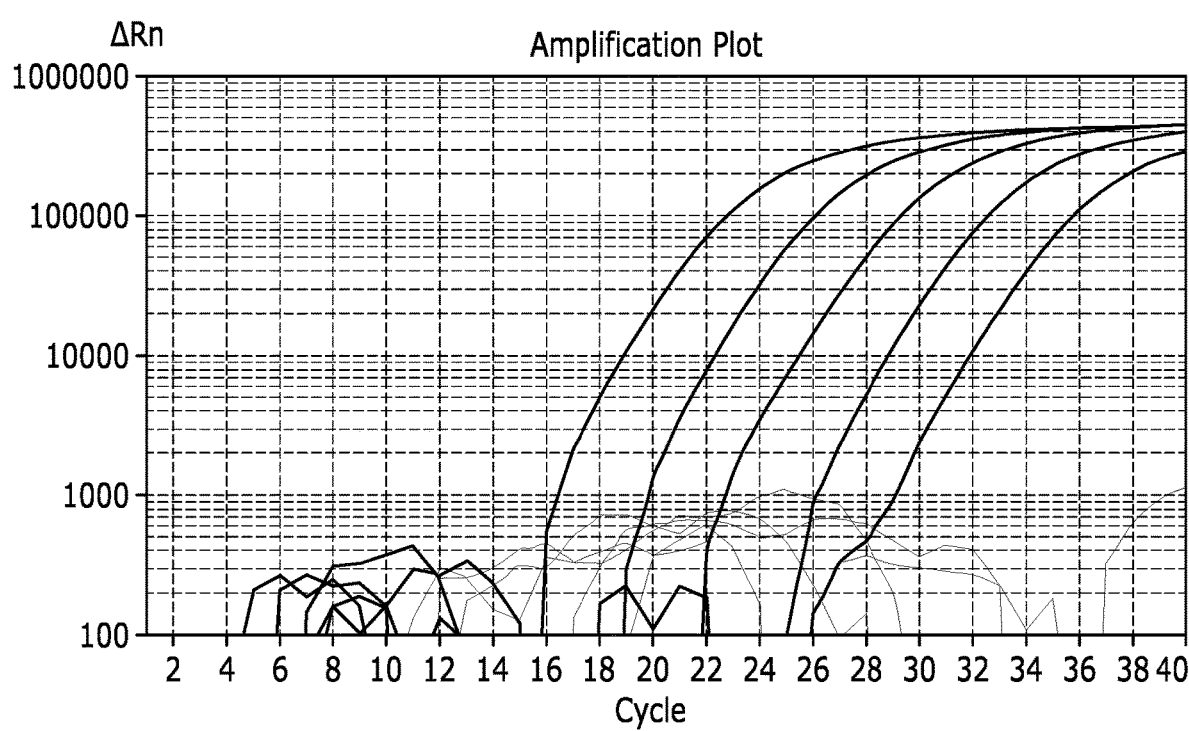
FIG. 6C

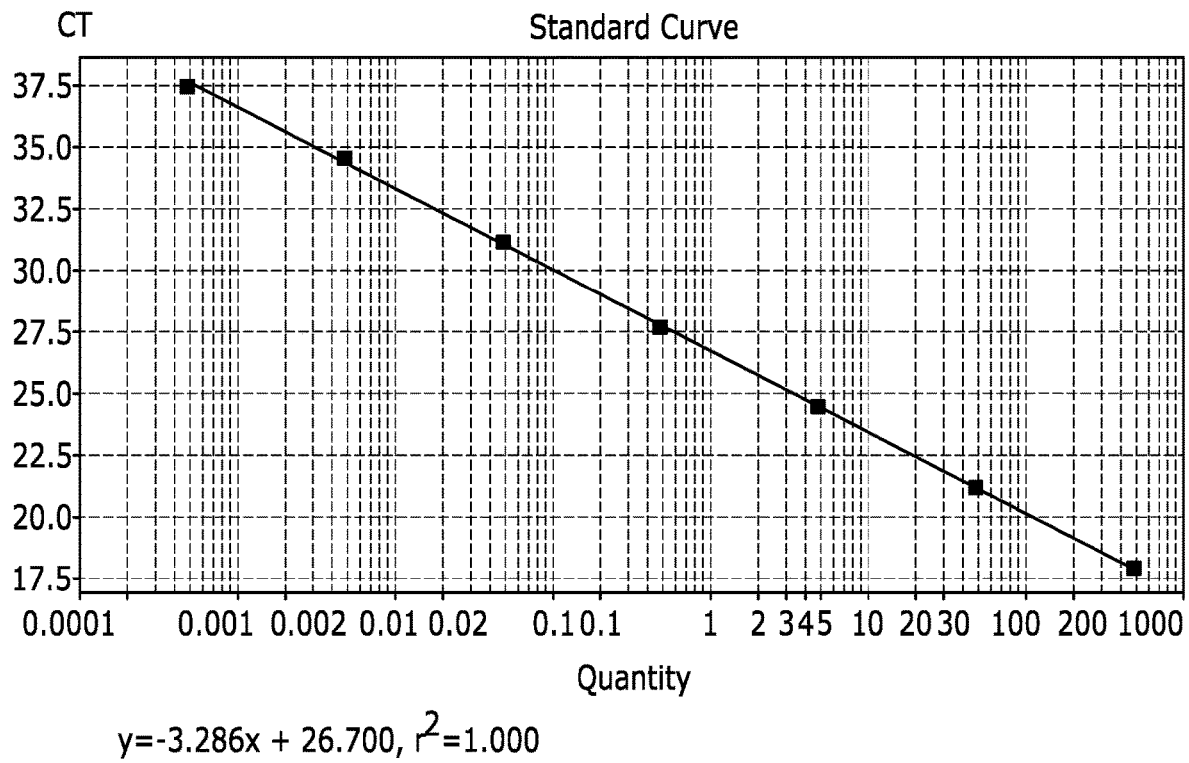
$y=-3.286x + 26.700, r^2=1.000$
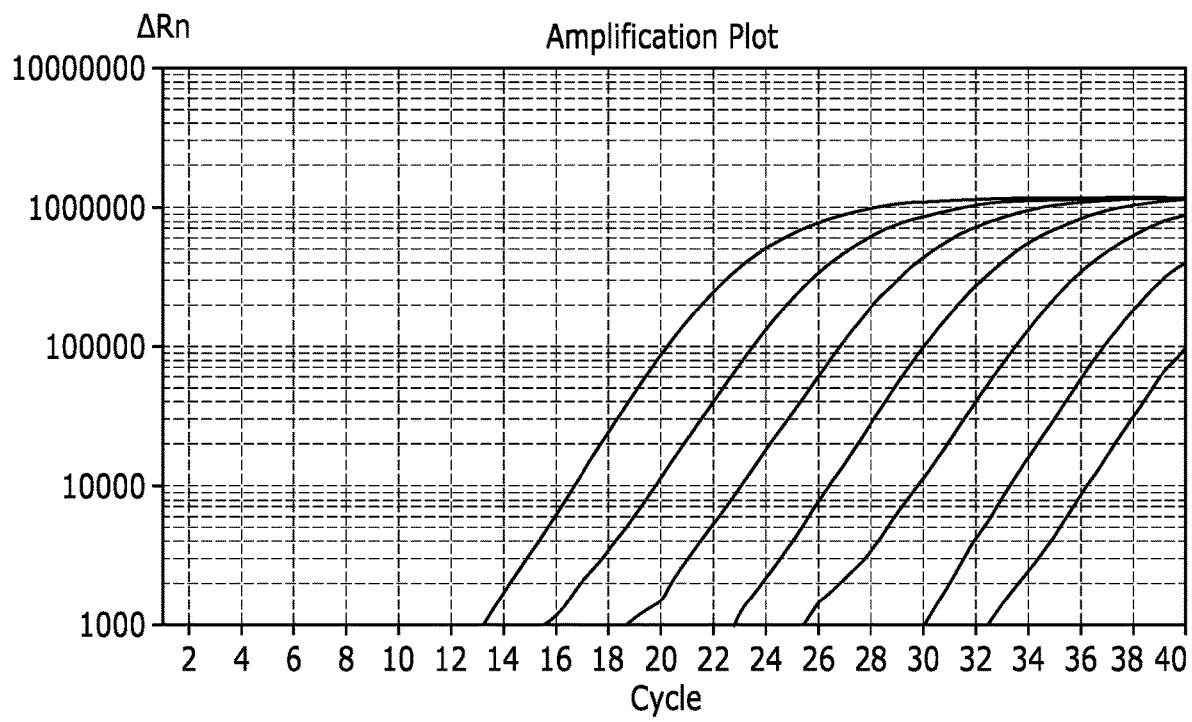
FIG. 6D

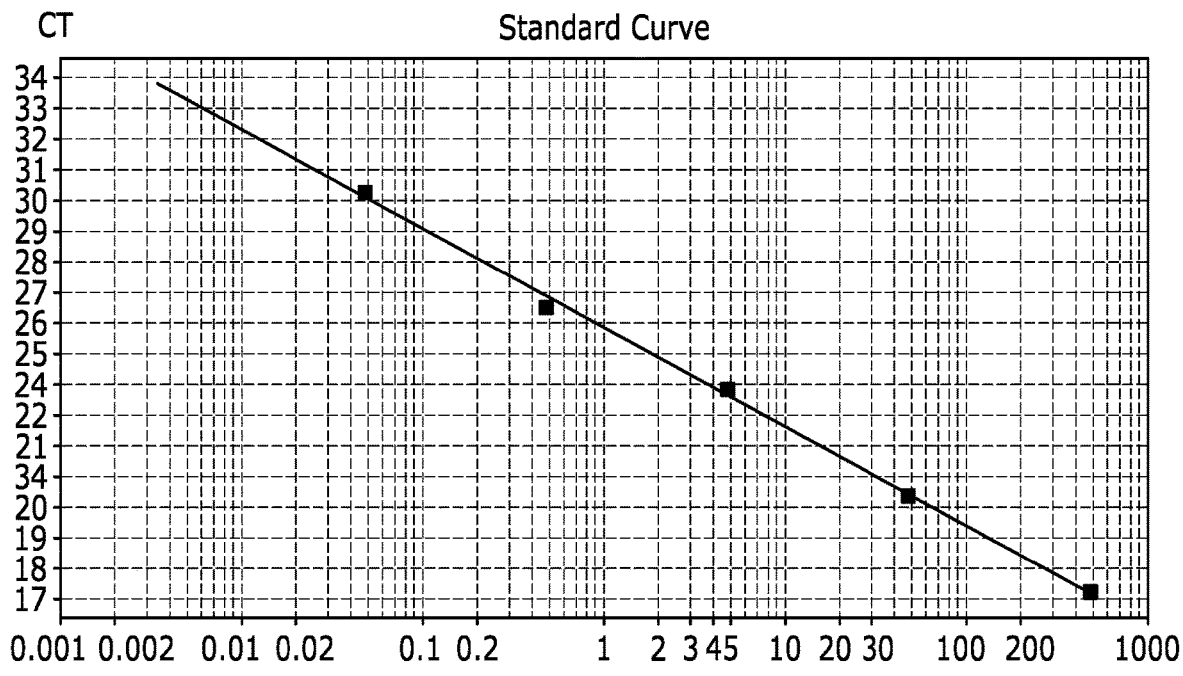
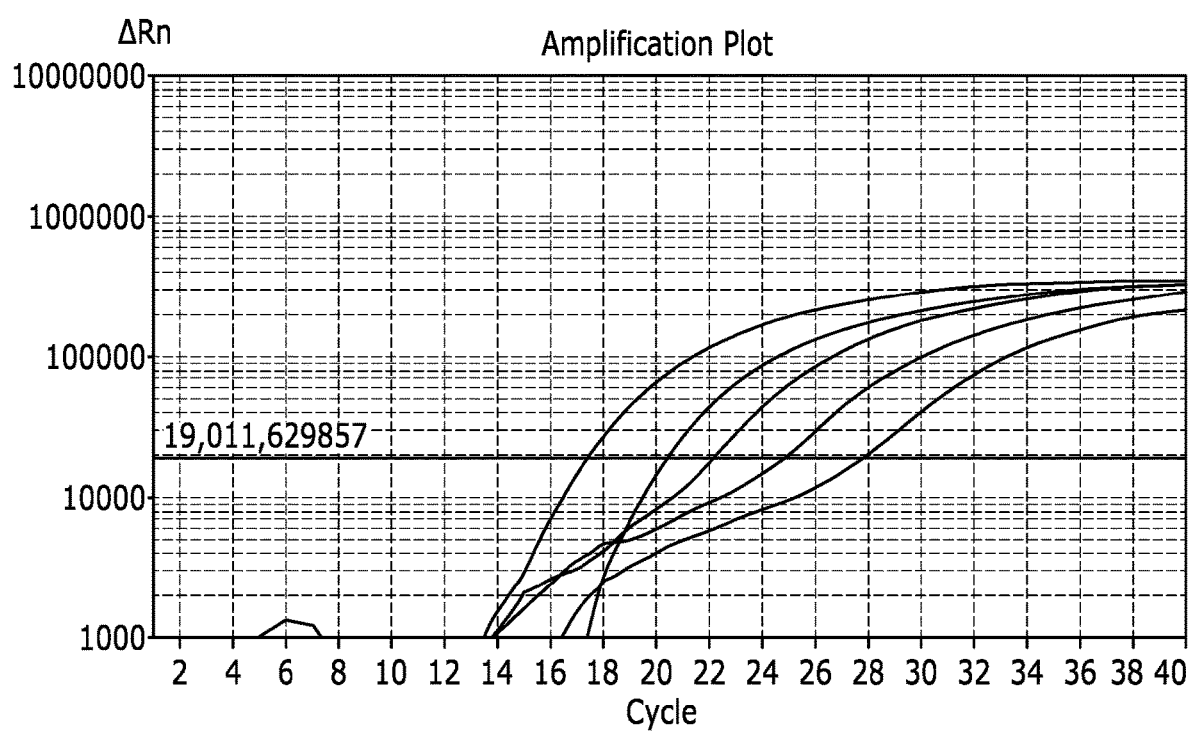
FIG. 6E

COMPOSITION, METHOD, AND SYSTEM FOR A RAPID, REAL-TIME PENTAPLEX PCR ASSAY FOR MAJOR BETA-LACTAMASE GENES

CROSS-REFERENCES TO RELATED APPLICATIONS

This application claims priority to U.S. Provisional Patent Application No. 63/148,520 entitled "PENTAPLEX REAL-TIME PCR ASSAY FOR RAPID IDENTIFICATION OF MAJOR BETA-LACTAMASE GENES KPC, NDM, CTX, CMY, AND OXA-48 DIRECTLY FROM BACTERIA IN BLOOD and filed on Feb. 11, 2021, naming Richard A. Robison, and Taalin Hoj as inventors. The content and subject matter of this patent application is hereby incorporated by reference in its entirety, including all text and drawings which is incorporated herein by reference.

FUNDING INFORMATION

Funding was provided by the National Institutes of Health (NIAID 1R01AI116989-01).

SEQUENCE LISTING

The instant application also contains a Sequence Listing which has been submitted electronically in ASCII format and is hereby incorporated by reference in its entirety. The ASCII copy, created on Feb. 8, 2022, is named 2200-2-24US_Feb0822_ST25.txt and is 3438 bytes in size.

FIELD OF THE INVENTION

This invention relates to blood-based assays for antibiotic resistant bacteria and more particularly relates to a real-time pentaplex assay for Carbapenem-resistant Enterobacteriaceae (CRE).

BACKGROUND

Antibiotic resistance, particularly in cases of sepsis, has emerged as a growing global public health concern and economic burden. Considered a pillar of modern medicine, antimicrobials have transformed the treatment of bacterial infections that were once fatal. However, as early as the 1940s, reports of microbial resistance to commonly used antibiotics surfaced, marking the rise of what is feared to become the post-antibiotic era. Today, 70% of bacterial infections are resistant to at least one commonly used antibiotic.

Current methods of blood culture and antimicrobial susceptibility testing of agents involved in sepsis can take as long as 3-5 days. CRE infections are notoriously challenging to treat, as these bacteria are generally resistant to most of the common antibiotics, including those of last resort such as the carbapenems and colistin. Septicemia from CREs has rapidly emerged and contributed to severe infections and deaths worldwide. In one study, survival rates were shown to decrease by 9% every hour that effective antimicrobial treatment is delayed. In another study, even when onset of active antimicrobial therapy for bacteremia resulting from CRE infection occurred within 47 hours, sepsis caused by CRE organisms resulted in a 49% mortality rate within 30 days. Another study concluded that patients with CRE-induced septicemia had a mortality rate of 63.8%, as compared to a non-CRE septicemia mortality rate of 33.4%.

Encouragingly, it has been observed that the rapid identification of resistant organisms (ideally within 1-3 hours of diagnosis of sepsis or septic shock) and instigation of effective antimicrobial treatment in sepsis patients can result in survival rates of 80%.

The current method of determining antimicrobial susceptibility for organisms causing sepsis can require up to 3-5 days, during which blood is drawn from the patient, the organism is cultured, and then is exposed to a panel of antimicrobials to determine the organism's resistance profile. This culture-based methodology is susceptible to contamination by common skin flora, cannot be used to identify uncultivatable organisms, and is limited by low bacterial counts in blood samples.

While waiting for results of the susceptibility testing, practitioners generally prescribe broad-spectrum antibiotics and only deescalate to targeted narrow-spectrum antibiotics once speciation and antibiotic susceptibilities are known. This strategy of employing empiric antibiotics often results in use of overly broad antibiotic exposure, which in turn contributes to resistance in microbial populations and decreased likelihood of successful treatment in the future.

Additional factors that contribute to the difficultly of timely appropriate treatment of sepsis caused by CREs are the low bacterial numbers present in blood samples, which are generally between 1-10 c.f.u. ml-1, and interference from components of formed elements present in whole blood such as haemoglobin. Using PCR-based methods to rapidly identify bacteria from whole blood has historically been difficult due to sensitivity loss in multiplex assays and formed element interference. Although commercially available assays exist to quickly diagnose bloodstream infections, these have limited usefulness these in a clinical setting.

For example, the Biofire BCID2 Panel requires a positive blood culture before the panel can be run; it also does not test for the presence of AmpC beta-lactamases. The T2Resistance Panel RUO requires five hours for sample identification, while the recommended time for sample identification is three hours or less. Other methods such as the EDTA-modified carbapenem inactivation method (eCIM) and the modified Hodge test require bacterial culture and may result in misclassifying strains that express both a carbapenemase and an AmpC or extended-spectrum beta-lactamase (ESBL).

Commercially available multiplex immunochromatographic assays do not test for ESBL or AmpC beta-lactamases. ESBL, AmpC beta-lactamases, and other carbapenem-hydrolysing enzymes such as oxacillinases are also not detected by most currently available assays, thereby overlooking common resistance genes involved in many antibiotic-resistant bloodstream infections. Additionally, each carbapenemase, ESBL, AmpC, and oxacillinase enzyme provides resistance to specific antimicrobials, due to differences in the enzyme active sites. Therefore, specific knowledge of the present beta-lactamase(s) is necessary to enable more targeted and effective treatments. It is also quite common for a single CRE to carry multiple drug resistance genes, which necessitates treatment by a combination of antimicrobials specific to the individual enzymes present in an organism.

Septicemia caused by carbapenem-resistant bacteria has a death rate of 40-60%. Therefore, rapid identification of which antimicrobials effectively treat sepsis cases on an individual basis is vital and a need exists for a composition, system, and method providing rapid diagnosis of antibiotic susceptibility directly from bacteria in blood by identification of beta-lactamase genes. Beneficially, such a composition, system and method would simultaneously assay for the most common beta lactamase genes in drug resistant bacteria.

SUMMARY

The present invention has been developed in response to the present state of the art, particularly in response to the problems and needs in the art that have not yet been fully solved by currently available blood-based assays. Accordingly, the present invention has been developed to provide a composition, method, and system for assaying antibiotic resistant bacteria that overcome many or all of the above-discussed shortcomings in the art.

Provided herein is composition for real-time amplification of DNA from at least one of beta-lactamase genes *Klebsiella pneumoniae* carbapenemase (KPC), New Delhi metallo-beta-lactamase (NDM), cefotaximase-Munich (CTX), cephamycin AmpC beta-lactamase (CMY), and oxacillinase-48 (OXA-48). In certain embodiments, the composition comprises at least one of a PCR primer pair with the sequence of SEQ. ID NOS 1-2, SEQ. ID Nos 4-5, SEQ. ID NOS 7-8, SEQ. ID NOS 10-11 SEQ. ID NOS 13-14.

Further provided herein is a composition for real-time detection of amplified DNA from at least one of beta-lactamase genes *Klebsiella pneumoniae* carbapenemase (KPC), New Delhi metallo-beta-lactamase (NDM), cefotaximase-Munich (CTX), cephamycin AmpC beta-lactamase (CMY), and oxacillinase-48 (OXA-48). In various embodiments, the composition omprises at least one of a probe with the sequence of SEQ. ID NO 3, SEQ. ID NO 6, SEQ. ID NO 9, SEQ. ID No 12, SEQ. ID No 15. The probe may comprise a detectable label which is sometimes a fluorophore. In some embodiments, the detectable label is selected based on emission spectra of each fluorophore. The probe may further comprise a quencher specific to the fluorophore.

Also provided herein is a method for detecting at least one of beta-lactamase genes KPC, NDM, CTX, CMY, and OXA-48 in a blood sample. In certain embodiments, the method comprises obtaining a blood sample from a subject and extracting bacterial cells from the blood sample. The bacterial cells may be isolated directly from blood according to U.S. Pat. No. 10,457,975. In some embodiments, the method further comprises providing at least one PCR primer pair, said pair comprising the sequence of least one of SEQ ID NO: 1-2, SEQ ID NO: 4-5, SEQ ID NO: 7-8, SEQ ID NO: 10-11, and SEQ ID NO 13-14. In various embodiments at least one PCR probe is provided, the probe comprising a detectable label and comprising the sequence of at least one of SEQ ID NO: 3, SEQ ID NO: 6, SEQ ID NO: 9, SEQ ID NO: 12 and SEQ ID NO: 15. According to the method herein the bacterial DNA may be amplified in a PCR reaction in the presence of the primer pairs and/or the probes. In various embodiments the bacterial cells, the five primer pairs, and the five probes are combined in a single tube pentaplex reaction. The method disclosed may further comprise reading the detectable label of the probe. The subject may be a human patient, sometimes suffering from septicemia.

Further provided herein is a system for detecting at least one of beta-lactamase genes KPC, NDM, CTX, CMY, and OXA-48 in a blood sample. In certain embodiments, the system comprises at least one PCR primer pair comprising the sequence of at least one of SEQ ID NO: 1-2, SEQ ID NO: 4-5, SEQ ID NO: 7-8, SEQ ID NO: 10-11, and SEQ ID NO 13-14. In some embodiments, the system comprises at least one probe comprising the sequence of at least one of SEQ ID NO: 3, SEQ ID NO: 6, SEQ ID NO: 9, SEQ ID NO: 12 and SEQ ID NO: 15. The probe may comprise a detectable label which is sometimes a fluorophore and may further comprise a quencher. In certain embodiments, the system herein comprises a pentaplex reaction comprising the five primer pairs and five associated probes. The system sometimes comprises PCR reaction reagents and/or laboratory apparatus.

Also disclosed herein is a kit for detecting at least one of beta-lactamase genes KPC, NDM, CTX, CMY, and OXA-48 in a blood sample. In some embodiments the kit comprises at least one primer pair having the sequence of least one of SEQ ID SEQ ID NO: 1-2, SEQ ID NO: 4-5, SEQ ID NO: 7-8, SEQ ID NO: 10-11, and SEQ ID NO 13-14. and comprising at least one probe having the sequence of at least one of SEQ ID NO: 3, SEQ ID NO: 6, SEQ ID NO: 9, SEQ ID NO: 12 and SEQ ID NO: 15. The kit may further comprise PCR reaction reagents and/or instructions for use.

Reference throughout this specification to features or similar language does not imply that all of the features that may be realized with the present invention should be or are in any single embodiment of the invention. Rather, language referring to the features is understood to mean that a specific feature or characteristic described in connection with an embodiment is included in at least one embodiment of the present invention. Thus, discussion of the features and characteristics, and similar language, throughout this specification may, but do not necessarily, refer to the same embodiment.

Furthermore, the described features, and characteristics of the invention may be combined in any suitable manner in one or more embodiments. One skilled in the relevant art will recognize that the invention can be practiced without one or more of the specific features or characteristics of a particular embodiment. In other instances, additional features and characteristics may be recognized in certain embodiments that may not be present in all embodiments of the invention.

These features and characteristics of the present invention will become more fully apparent from the following description and appended claims, may be learned by the practice of the invention as set forth hereinafter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 is a table depicting isolates used to validate the assay and resistance genes present in each isolate in accordance with the present invention;

FIG. 2 is a table depicting Pentaplex primer and probe sequences;

FIG. 3 is a table depicting r2 values and sensitivities of each gene from culture in singleplex and pentaplex, or pentaplex from blood in accordance with the present invention;

FIG. 4(*a*) is a set of graphs depicting sensitivity of an individual target assay for the presence of KPC from the strain 0112 in accordance with the present invention;

FIG. 4(*b*) is a set of graphs depicting sensitivity of an individual target assay for the presence of NDM from the strain 0119 in accordance with the present invention;

FIG. 4(*c*) is a set of graphs depicting sensitivity of an individual target assay for the presence of CTX from the strain 0119 in accordance with the present invention;

FIG. 4(d) is a set of graphs depicting sensitivity of an individual target assay for the presence of CMY from the strain 0119 in accordance with the present invention;

FIG. 4(e) is a set of graphs depicting sensitivity of an individual target assay for the presence of OXA-48 from the strain 0160 in accordance with the present invention;

FIG. 5(a) is a set of graphs depicting sensitivity of the pentaplex assay from bacterial culture for the presence of KPC from the strain 0112 in accordance with the present invention;

FIG. 5(b) is a set of graphs depicting sensitivity of the pentaplex assay from bacterial culture for the presence NDM from the strain 0119 in accordance with the present invention;

FIG. 5(c) is a set of graphs depicting sensitivity of the pentaplex assay from bacterial culture for the presence CTX from the strain 0119 in accordance with the present invention;

FIG. 5(d) is a set of graphs depicting sensitivity of the pentaplex assay from bacterial culture for the presence CMY from the strain 0119 in accordance with the present invention;

FIG. 5(e) is a set of graphs depicting sensitivity of the pentaplex assay for the presence of OXA-48 from the strain 0160 in accordance with the present invention;

FIG. 6(a) is a set of graphs depicting sensitivity of pentaplex assay in bacteria derived from blood for the presence of KPC from the strain 0112 in accordance with the present invention;

FIG. 6(b) is a set of graphs depicting sensitivity of pentaplex assay in bacteria derived from blood for the presence of NDM from the strain 0119 in accordance with the present invention;

FIG. 6(c) is a set of graphs depicting sensitivity of pentaplex assay in bacteria derived from blood for the presence of CTX the strain 0119 in accordance with the present invention;

FIG. 6(d) is a set of graphs depicting sensitivity of pentaplex assay in bacteria derived from blood for the presence of CMY the strain 0119 in accordance with the present invention;

FIG. 6(e) is a set of graphs depicting sensitivity of pentaplex assay in bacteria derived from blood for the presence of OXA-48 from the strain 0160 in accordance with the present invention;

DETAILED DESCRIPTION OF THE INVENTION

Figure 7:
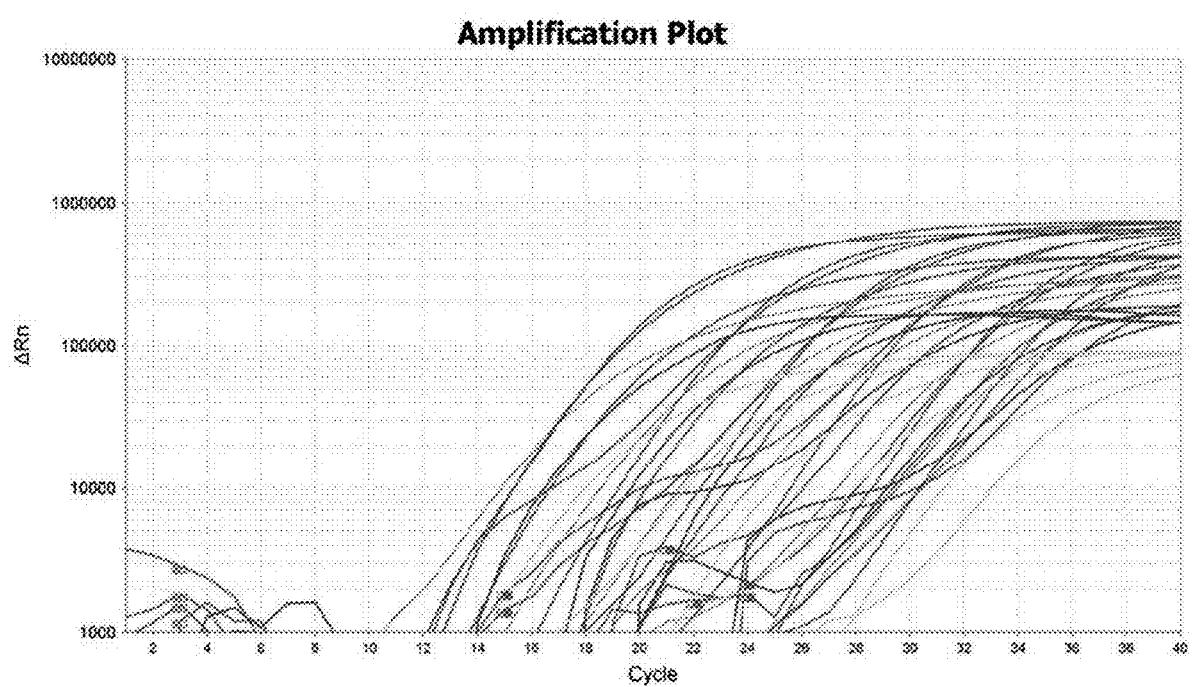
FIG. 7 is an amplification plot depicting simultaneous amplification of all five beta-lactamase gene targets in the pentaplex format in accordance with the present invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

Provided herein are primers and probes which can identify all subtypes of *Klebsiella pneumoniae* carbapenemase (KPC); New Delhi metallo-beta-lactamase (NDM); cefotaximase-Munich (CTX); cephamycin AmpC beta-lactamase (CMY); and oxacillinase-48 (OXA-48).

Therefore, it is possible according to this invention to identify in real time the major beta-lactamase genes present in bacteria isolated directly from blood. This quantitative PCR assay was able to concurrently identify the five most common beta-lactamase genes (KPC, NDM, CTX, CMY, and OXA-48) in a single-tube reaction format with no loss of sensitivity due to multiplexing. Consequently, this assay is capable of rapid, precise identification of the major beta-lactamase genes present in bacteria taken directly from blood, requiring no blood culturing. These results can be available in under 2 hours from blood having bacterial concentrations down to 4 c.f.u. ml-$^1$.

In the United States, most carbapenem-resistant blood infections are caused by organisms carrying either KPC or NDM; these organisms also commonly carry multiple ESBL, AmpC, or oxacillinase (OXA) genes. The most common ESBL gene present in resistant pathogens in the United States is Cefotaximase-Munich (CTX), while the most common AmpC gene is CMY. Oxacillinase-48 is a less common enzyme but is present in many antibiotic-resistant isolates and is capable of hydrolysing carbapenems and other commonly used antibiotics.

FIG. 1 (Table 1) depicts isolates used to validate assay and resistance genes present in each isolate according to the present invention. The isolates listed in Table 1 were obtained from the Centre for Disease Control Antibiotic Resistance Isolate Bank Enterobacterales Carbapenemase Diversity Panel and were used to develop and validate this assay. Stock cultures of each isolate were grown on Luria broth (LB) agar plates containing 8 μg ml-$^1$ imipenem, then incubated at 37° C. for 24 h. Plates were stored at 4° C.

A "+" indicates the presence of a beta-lactamase gene in the given isolate. Beta-lactamase target genes were present in at least one strain of bacteria, with CMY present in seven strains, KPC and NDM in six strains, CTX in two strains and OXA-48 in one strain.

FIG. 2 (Table 2) depicts the novel primer and probe sequences used to test for each of KPC, NDM, CTX, CMY, and OXA-48 genes according to the present invention. _F indicates a forward primer; _R indicates a reverse primer; _Pro indicates a probe; BHQ1 indicates Black Hole Quencher 1; BHQ2 indicates Black Hole Quencher 2; and IBRQ, indicates Iowa Black R Quencher. The novel primer and probe sequences provided herein yield pentaplex assay sensitivities at least substantially comparable to individual assays performed for each beta-lactamase gene.

FIG. 3 (Table 3) indicates the $r^2$ values and sensitivities of each beta lactamase gene assay from culture in singleplex and pentaplex, or pentaplex from blood according to the present invention. The bacteria-blood separation technology removes interfering elements from the blood, which allows the pentaplex qPCR assay to detect low levels of bacterial DNA targets typically present in blood samples from patients with early bacteremias. Additionally, this assay returns results within the desired 1 to 3 h range for septicemia identification and is effective in a single-tube format without losing sensitivity due to multiplexing, a common problem for many multiplex PCR assays. Using the results from this assay in conjunction with existing methods for bacterial identification and antibiotic susceptibility may help inform increasingly effective treatment options for patients presenting with septicemia.

FIGS. 4(a), (b), (c), (d), and (e) depict a standard curve and an amplification plot for the sensitivities of individual target assays according to the present invention. Serial tenfold dilutions of CRE DNA containing the desired target genes were tested in a singleplex reaction to determine the detection limit for each of: (a) KPC, from strain 0112; (b) NDM, strain 0119; (c) CTX, strain 0119; (d) CMY, strain 0119; and (e) OXA-48, strain 0160. Individual runs with different DNA concentrations provided Ct values which were plotted against the log of the concentration of DNA to obtain the standard curve. DNA quantity was adjusted to 481 µg ml-$^1$ for each starting concentration. The assays demonstrated similar sensitivities.

FIGS. 5(a), (b), (c), (d), and (e) depict a standard curve and an amplification plot for sensitivities of the pentaplex assay for target genes from bacteria in culture according to the present invention. Serial tenfold dilutions of CRE DNA containing the desired target gene(s) were tested in a single tube format as a pentaplex reaction. Target genes were: (a) KPC, from strain 0112; (b) NDM, strain 0119; (c) CTX, strain 0119; (d) CMY, strain 0119; and (e) OXA-48, strain 0160. Individual runs with different DNA concentrations provided Ct values which were plotted against the log of the concentration of DNA to obtain the standard curve. DNA quantity was adjusted to 481 µg ml-$^1$ for each starting concentration. The pentaplex assay yielded sensitivities substantially comparable to individual assays for beta-lactamase DNA.

FIG. 6 depicts sensitivities of pentaplex assay for target gene DNA in bacteria derived from blood according to the present invention. Serial tenfold dilutions of CRE DNA containing the desired target gene(s) were tested in a single tube format as a pentaplex reaction. Targeted genes were: (a) KPC, from strain 0112; (b) NDM, strain 0119; (c) CTX, strain 0119; (d) CMY, strain 0119; and (e) OXA-48, strain 0160. Individual runs with different DNA concentrations provided Ct values which were plotted against the log of the concentration of DNA to obtain the standard curve. DNA quantity was adjusted to 481 µg ml-$^1$ for each starting concentration. The pentaplex assay yielded sensitivities substantially comparable to individual assays for target gene DNA.

FIG. 7 depicts an amplification plot showing simultaneous amplification of all five beta-lactamase gene targets in the pentaplex format. Red represents KPC (strain 0112); green represents CMY (strain 0119); blue represents NDM (strain 0119); yellow represents CTX (strain0119); grey represents OXA-48 (strain 0160). As illustrated, the compositions and methods of the invention herein identify the major beta-lactamase genes present in bacteria isolated directly from blood.

This quantitative PCR assay was able to concurrently amplify and identify the five most common beta-lactamase genes (KPC, NDM, CTX, CMY, and OXA-48) in a single-tube reaction format with no loss of sensitivity due to multiplexing. The assay provided herein can be completed in under 2 hours using DNA from bacteria taken directly from blood, requiring no blood culturing, and identifies the most common beta-lactamase genes present in bacteria that cause bloodstream infections in the United States. Detection limits are as low as four genome copies, i.e. 4 c.f.u. ml-$^1$, per blood sample.

The information provided by this assay may improve patient care and outcomes by allowing for early CRE detection and characterization. In combination with other technologies such as tests for vancomycin resistance, this assay may promote the utilization of antibiotics which can successfully treat multi-drug resistant infections, improving the current bleak survival rates of bacteremias caused by these organisms.

EXAMPLES

Example 1: DNA Preparation

A single colony from a stock plate of each isolate was used to inoculate 10 ml LB containing 8 µg ml-$^1$ imipenem at 37° C. in a non-shaking incubator. Bacteria were allowed to grow for 12 hours to an OD reading of 1, roughly 2×10$^9$ c.f.u. ml-$^1$. Total genomic DNA was extracted from each isolate from 1 ml of culture suspension using the DNeasy UltraClean Microbial Kit (Qiagen). DNA concentration was measured using an ND-1000 spectrophotometer (Nanodrop Technologies). The DNA concentration before dilution averaged 4800 µg ml-$^1$.

Example 2: Primer and Probe Design and Testing

Quantitative PCR assays for each beta-lactamase gene using 5'-hydrolysis Taqman probes were designed using Clustal Omega and software available from Integrated DNA Technologies. Fluorophores were chosen based on emission spectra of each fluorophore. Eighty sequences for each beta-lactamase gene subtype were obtained from NCBI and aligned using the Clustal Omega software. The BLASTN programme at the National Centre for Biotechnology Information (NCBI) and the Clustal Omega software confirmed that the PCR target regions were specific to each gene and covered the most common single-nucleotide polymorphism subtypes for each gene (i.e. the PCR target regions for KPC target KPC-2, KPC-3, etc.), but did not target other genes such as CTX. Blind tests were conducted using a random numbering system of the target DNA from each isolate listed in Table 1 (FIG. 1). These tests were used to test sensitivity and detect false positives, false negatives, and ensure accurate identification of each target gene. No false positives or false negatives were found, and each target was accurately identified each time.

The assay indicated similar sensitivity, regardless of the isolate from which the DNA was obtained. Replicates for each gene were repeated 3-6 times. Difficulties commonly faced when designing multiplex PCR assays, such as differing primer annealing temperatures and inter-region differences in GC content were overcome by careful design of novel primers and analysis of the surrounding regions of the primers and probes. The primer and probe sequences used are listed in Table 2 (FIG. 2). Primers and probes were purchased from Integrated DNA Technologies.

Example 3: PCR Cycling Conditions

Quantitative PCR assays were performed on a QuantStudio five using Integrated DNA Technology's PrimeTime Gene Expression Master Mix. Individual assay conditions were 500 nM forward primer, 500 nM reverse primer, 250 nM probe, 50 ng target DNA, and HPLC-grade H$^2$O for a final assay volume of 20 µl. Pentaplex reaction conditions were the same for each target gene, except no water was added. The final sample volume for pentaplex reactions was 25.2 μl. Thermal cycling conditions were 5 min at 95° C., followed by 40 cycles of 5 seconds at 95° C. and 30 seconds at 70° C. and a post-read cycle of 30 seconds at 60° C. A positive signal was determined by QuantStudio five threshold software before cycle 22. Cycle 22 was chosen because it was the latest cycle that the positive control samples amplified the target gene. The baseline and threshold settings used were the standard default values on the QuantStudio five platform.

Example 4: Separating Bacteria from Blood and Bacterial DNA Isolation

Whole human blood was obtained from volunteers (BYU IRBNo.: X18-340) by venipuncture into EDTA tubes and spiked with a dilution of the bacterial cultures prepared as described above. The final concentration of bacteria in the spiked blood samples was about 10 c.f.u. ml$^{-1}$. Bacteria were separated from human blood using the spinning disc method of U.S. Pat. No. 10,457,975 previously described by Buchanan et al. This spinning disc method utilizes novel separation technology that exploits the subtle size and density differences between erythrocytes and bacterial cells, which conventional centrifugation does not.

Following plasma collection, samples were added to microcentrifuge tubes and lysozyme (0.5 mg ml$^{-1}$, Sigma-Aldrich, chicken egg white #L6876) was added to each tube, vortexed for 5 seconds, then incubated for 10 minutes at room temperature. One hundred microlitres each of 6 M guanidine HCl (Promega, #H5381) solution and 1% sodium dodecyl sulphate (SDS, USB #18220) solution was then added to each microcentrifuge tube and vortexed for 30 seconds. Following lysis, 200 μl of isopropanol and 25 μl of Spherotech magnetic beads (#SIM-05-10 h) were added to each microcentrifuge tube, which were vortexed for 30 seconds and placed on a magnet holder. Beads were allowed to aggregate on the side of the tube wall adjacent to the magnet for two minutes at which time the liquid was removed. Then 450 μl of Wash 1 solution (6 M guanidine isothiocyanate, 20 mM Tris-HCl, v/v isopropanol, balance water) was added to each microcentrifuge tube and the tubes were vortexed for 30 seconds before being placed back in the magnet holder. Beads were aggregated and after 2 minutes, Wash 1 solution was removed and Wash 2 solution (0.1 M NaCl, 10 mM Tris-HCl, 70% v/v ethanol, balance water) was added. The tubes were vortexed again for 30 seconds, placed back in the magnet holder, and beads allowed to aggregate for 2 minutes. Wash 2 solution was removed and the tubes were air-dried for 5 minutes. Fifteen microlitres of EDTA elution buffer solution (1 mM EDTA in water) was added and tubes were vortexed for 2 minutes to allow the DNA to detach from the beads for final resuspension in the elution buffer solution. The microcentrifuge tubes were placed back in the magnet holder for 1 minute, after which the solutions were placed in clean microcentrifuge tubes. DNA was then serially diluted for further analysis via qPCR. The bacterial separation and DNA extraction took approximately 25 minutes, while the time to prepare and run the qPCR was about an hour. Combined, this process required almost 1.5 hour from time of blood sample collection to reading the assay results.

Example 5: Pentaplex Detection Sensitivity in Bacteria Derived from Pure Culture and from Blood Serial tenfold dilutions of whole genomic DNA from clinical CRE isolates were used for optimization of primer and probe sets. Many iterations were performed to arrive at a successful combination of the five individual assays into a single tube, pentaplex reaction. FIG. 5 shows the sensitivity of the pentaplex reaction using DNA from pure cultures. FIG. 6 shows the performance of the pentaplex reaction using DNA extracted from bacteria in blood. The sensitivities of the individual assays did not decrease when combined into the final single reaction, whether the DNA was from pure cultures (FIG. 5), or from bacteria present in blood (FIG. 6). To prove that the concurrent presence of all target genes in a pentaplex reaction did not decrease the sensitivities of any of the individual assays, all five genes were combined into a pentaplex reaction in a single tube. Gene targets were present in three different bacteria which were spiked into human blood. Following separation, extraction, and serial tenfold dilution, each target gene amplified in the pentaplex reaction at the same rate as when run in a single reaction. The assay's successful identification of all five targets concurrently also confirmed no fluorophore interference (FIG. 7). See Table 3 (FIG. 3) for r2 values and sensitivities of each gene in pentaplex with each gene target present.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A composition for real-time amplification and detection of bacterial DNA in a single tube pentaplex reaction, the DNA being individually specific to at least one of beta-lactamase genes Klebsiella pneumoniae carbapenemase (KPC); New Delhi metallo-beta-lactamase (NDM); cefotaximase-Munich (CTX); cephamycin AmpC beta-lactamase (CMY); and oxacillinase-48 (OXA-48), the composition consisting of:
  a first primer pair consisting of sequences according to SEQ ID NO: 1 and SEQ ID NO: 2, and a first probe consisting of a sequence according to SEQ ID NO: 3 and a detectable label, wherein the first primer pair amplifies a nucleotide sequence that encodes the KPC gene;
  a second primer pair consisting of sequences according to SEQ ID NO: 4 and SEQ ID NO: 5, and a second probe consisting of a sequence according to SEQ ID NO: 6 and a detectable label, wherein the second primer pair amplifies a nucleotide sequence that encodes the NDM gene;
  a third primer pair consisting of sequences according to SEQ ID NO: 7 and SEQ ID NO: 8, and a third probe consisting of a sequence according to SEQ ID NO: 9 and a detectable label, wherein the third primer pair amplifies a nucleotide sequence that encodes the CTX gene;
  a fourth primer pair consisting of sequences according to SEQ ID NO: 10 and SEQ ID NO: 11, and a fourth probe consisting of a sequence according to SEQ ID NO: 12 and a detectable label, wherein the fourth primer pair amplifies a nucleotide sequence that encodes the CMY gene; and
  a fifth primer pair consisting of sequences according to SEQ ID NO: 13 and SEQ ID NO: 14, and a fifth probe consisting of a sequence according to SEQ ID NO: 15 and a detectable label, wherein the fifth primer pair amplifies a nucleotide sequence that encodes the OXA-48 gene.

2. The composition of claim 1, wherein the detectable label is a fluorophore.

3. The composition of claim 2, wherein the detectable label is selected based on an emission spectrum of each fluorophore.

4. A system for detecting beta-lactamase genes in a blood sample in a single tube pentaplex reaction, the system comprising:
  a composition consisting of:
  a first primer pair consisting of sequences according to SEQ ID NO: 1 and SEQ ID NO: 2, and a first probe consisting of a sequence according to SEQ ID NO: 3, a detectable label that is a fluorophore, and a quencher specific to the fluorophore, wherein the first primer pair amplifies a nucleotide sequence that encodes a Klebsiella pneumoniae carbapenemase (KPC) gene,
  a second primer pair consisting of sequences according to SEQ ID NO: 4 and SEQ ID NO: 5, and a second probe consisting of a sequence according to SEQ ID NO: 6, a detectable label that is a fluorophore, and a quencher specific to the fluorophore, wherein the second primer pair amplifies a nucleotide sequence that encodes a New Delhi metallo-beta-lactamase (NDM) gene,
  a third primer pair consisting of sequences according to SEQ ID NO: 7 and SEQ ID NO: 8, and a third probe consisting of a sequence according to SED ID NO: 9, a detectable label that is a fluorophore, and a quencher specific to the fluorophore, wherein the third primer pair amplifies a nucleotide sequence that encodes a cefotaximase-Munich (CTX) gene,
  a fourth primer pair consisting of sequences according to SEQ ID NO: 10 and SEQ ID NO: 11, and a fourth probe consisting of a sequence according to SEQ ID NO: 12, a detectable label that is a fluorophore, and a quencher specific to the fluorophore, wherein the fourth primer pair amplifies a nucleotide sequence that encodes a cephamycin AmpC beta-lactamase (CMY) gene, and
  a fifth primer pair consisting of sequences according to SEQ ID NO: 13 and SEQ ID NO: 14, and a fifth probe consisting of a sequence according to SEQ ID NO: 15, a detectable label that is a fluorophore, and a quencher specific to the fluorophore, wherein the fifth primer pair amplifies a nucleotide sequence that encodes an oxacillinase-48 (OXA-48) gene;
  wherein each probe comprises a detectable label.

5. The system of claim 4, further comprising PCR reaction reagents and/or laboratory apparatuses.

6. A kit for detecting beta-lactamase genes in a blood sample in a single tube pentaplex reaction, the kit comprising:
  a composition consisting of:
  a first primer pair consisting of sequences according to SEQ ID NO: 1 and SEQ ID NO: 2, and a first probe consisting of a sequence according to SEQ ID NO: 3 and a detectable label, wherein the first primer pair amplifies a nucleotide sequence that encodes a Klebsiella pneumoniae carbapenemase (KPC) gene,
  a second primer pair consisting of sequences according to SEQ ID NO: 4 and SEQ ID NO: 5, and a second probe consisting of a sequence according to SEQ ID NO: 6 and a detectable label, wherein the second primer pair amplifies a nucleotide sequence that encodes a New Delhi metallo-beta-lactamase (NDM) gene,
  a third primer pair consisting of sequences according to SEQ ID NO: 7 and SEQ ID NO: 8, and a third probe consisting of a sequence according to SED ID NO: 9 and a detectable label, wherein the third primer pair amplifies a nucleotide sequence that encodes a cefotaximase-Munich (CTX) gene,
  a fourth primer pair consisting of sequences according to SEQ ID NO: 10 and SEQ ID NO: 11, and a fourth probe consisting of a sequence according to SEQ ID NO: 12 and a detectable label, wherein the fourth primer pair amplifies a nucleotide sequence that encodes a cephamycin AmpC beta-lactamase (CMY) gene, and a fifth primer pair consisting of sequences according to SEQ ID NO: 13 and SEQ ID NO: 14, and a fifth probe consisting of a sequence according to SEQ ID NO: 15 and a detectable label, wherein the fifth primer pair amplifies a nucleotide sequence that encodes an oxacillinase-48 (OXA-48) gene;

wherein each probe comprises a detectable label.

7. The kit of claim 6, further comprising PCR reaction reagents.

8. The kit of claim 7, further comprising instructions for use.

\* \* \* \* \*

SEQUENCE LISTING

<160> NUMBER OF SEQ ID NOS: 15

<210> SEQ ID NO 1
<211> LENGTH: 26
<212> TYPE: DNA
<213> ORGANISM: Artificial Sequence
<220> FEATURE:
<223> OTHER INFORMATION: KPC_F* beta-lactamase gene primer/probe

<400> SEQUENCE: 1
ccgtctagtt ctgctgtctt gtctct                                    26

<210> SEQ ID NO 2
<211> LENGTH: 25

-continued

```
<212> TYPE: DNA
<213> ORGANISM: Artificial Sequence
<220> FEATURE:
<223> OTHER INFORMATION: KPC_R beta-lactamase gene primer/probe

<400> SEQUENCE: 2
gccaaagtcc tgttcgagtt tagcg                                         25

<210> SEQ ID NO 3
<211> LENGTH: 29
<212> TYPE: DNA
<213> ORGANISM: Artificial Sequence
<220> FEATURE:
<223> OTHER INFORMATION: KPC_Pro beta-lactamase gene primer/probe

<400> SEQUENCE: 3
gctggctttt ctgccaccgc gctgaccaa                                     29

<210> SEQ ID NO 4
<211> LENGTH: 22
<212> TYPE: DNA
<213> ORGANISM: Artificial Sequence
<220> FEATURE:
<223> OTHER INFORMATION: NDM_F beta-lactamase gene primer/probe

<400> SEQUENCE: 4
ggtttgatcg tcagggatgg cg                                            22

<210> SEQ ID NO 5
<211> LENGTH: 23
<212> TYPE: DNA
<213> ORGANISM: Artificial Sequence
<220> FEATURE:
<223> OTHER INFORMATION: NDM_R beta-lactamase gene primer/probe

<400> SEQUENCE: 5
ggcaggttga tctcctgctt gat                                           23

<210> SEQ ID NO 6
<211> LENGTH: 32
<212> TYPE: DNA
<213> ORGANISM: Artificial Sequence
<220> FEATURE:
<223> OTHER INFORMATION: NDM_Pro beta-lactamase gene primer/probe

<400> SEQUENCE: 6
tgctggtggt cgataccgcc tggaccgatg ac                                 32

<210> SEQ ID NO 7
<211> LENGTH: 18
<212> TYPE: DNA
<213> ORGANISM: Artificial Sequence
<220> FEATURE:
<223> OTHER INFORMATION: CTX_F beta-lactamase gene primer/probe

<400> SEQUENCE: 7
gtgtgccgct gtatgcgc                                                 18

<210> SEQ ID NO 8
<211> LENGTH: 33
<212> TYPE: DNA
<213> ORGANISM: Artificial Sequence
<220> FEATURE:
<223> OTHER INFORMATION: CTX_R beta-lactamase gene primer/probe

<400> SEQUENCE: 8
```
gcacgataaa gtatttgcga attatctgct gtg        33

<210> SEQ ID NO 9
<211> LENGTH: 30
<212> TYPE: DNA
<213> ORGANISM: Artificial Sequence
<220> FEATURE:
<223> OTHER INFORMATION: CTX_Pro beta-lactamase gene primer/probe

<400> SEQUENCE: 9
gccgaattag agcggcagtc gggaggcaga        30

<210> SEQ ID NO 10
<211> LENGTH: 24
<212> TYPE: DNA
<213> ORGANISM: Artificial Sequence
<220> FEATURE:
<223> OTHER INFORMATION: CMY_F beta-lactamase gene primer/probe

<400> SEQUENCE: 10
agcgacttta cgctaactcc agca        24

<210> SEQ ID NO 11
<211> LENGTH: 27
<212> TYPE: DNA
<213> ORGANISM: Artificial Sequence
<220> FEATURE:
<223> OTHER INFORMATION: CMY_R beta-lactamase gene primer/primer

<400> SEQUENCE: 11
cgtctggtca ttgcctcttc gtaactc        27

<210> SEQ ID NO 12
<211> LENGTH: 22
<212> TYPE: DNA
<213> ORGANISM: Artificial Sequence
<220> FEATURE:
<223> OTHER INFORMATION: CMY_Pro beta-lactamase gene primer/probe

<400> SEQUENCE: 12
tggcgcgctg gcggtgaaac cc        22

<210> SEQ ID NO 13
<211> LENGTH: 25
<212> TYPE: DNA
<213> ORGANISM: Artificial Sequence
<220> FEATURE:
<223> OTHER INFORMATION: OXA_F beta-lactamase gene primer/probe

<400> SEQUENCE: 13
gatatcgcca cttggaatcg cgatc        25

<210> SEQ ID NO 14
<211> LENGTH: 30
<212> TYPE: DNA
<213> ORGANISM: Artificial Sequence
<220> FEATURE:
<223> OTHER INFORMATION: OXA_R beta-lactamase gene primer/probe

<400> SEQUENCE: 14
ccataatcga aagcatgtag catcttgctc        30

<210> SEQ ID NO 15
<211> LENGTH: 26
<212> TYPE: DNA
<213> ORGANISM: Artificial Sequence

```
<220> FEATURE:
<223> OTHER INFORMATION: OXA_Pro beta-lactamase gene primer/probe

<400> SEQUENCE: 15
ttgcccgcca aattggcgag gcacgt                                           26
```